(12) United States Patent
Chen et al.

(10) Patent No.: US 10,193,083 B2
(45) Date of Patent: Jan. 29, 2019

(54) SPIRALLY CONFIGURED CIS-STILBENE/FLUORENE HYBRID COMPOUNDS AND ORGANIC LIGHT EMITTING DEVICE COMPRISING THE SAME

(71) Applicant: NICHEM FINE TECHNOLOGY CO., LTD., Jhubei, Hsinchu County (TW)

(72) Inventors: Chien-Tien Chen, Jhubei (TW); Chi-Chung Chen, Jhubei (TW)

(73) Assignee: NICHEM FINE TECHNOLOGY CO., LTD., Jhubei, Hsinchu County (TW)

(*) Notice: Subject to any disclaimer, the term of this patent is extended or adjusted under 35 U.S.C. 154(b) by 175 days.

(21) Appl. No.: 15/228,564

(22) Filed: Aug. 4, 2016

(65) Prior Publication Data

US 2017/0040547 A1     Feb. 9, 2017

Related U.S. Application Data

(60) Provisional application No. 62/200,929, filed on Aug. 4, 2015.

(51) Int. Cl.
*H01L 51/54* (2006.01)
*C09K 11/06* (2006.01)
(Continued)

(52) U.S. Cl.
CPC ........ *H01L 51/0072* (2013.01); *C07C 211/58* (2013.01); *C07C 255/52* (2013.01); *C07D 209/86* (2013.01); *C07D 213/06* (2013.01); *C07D 221/20* (2013.01); *C07D 235/02* (2013.01); *C07D 235/20* (2013.01); *C07D 251/24* (2013.01); *C07D 401/14* (2013.01); *C07D 403/14* (2013.01); *C07D 471/04* (2013.01); *C07D 471/10* (2013.01); *C07D 487/04* (2013.01); *C07F 5/027* (2013.01); *C07F 9/5329* (2013.01); *C09K 11/025* (2013.01); *C09K 11/06* (2013.01); *H01L 51/006* (2013.01); *H01L 51/008* (2013.01); *H01L 51/0052* (2013.01); *H01L 51/0056* (2013.01); *H01L 51/0058* (2013.01); *H01L 51/0061* (2013.01); *H01L 51/0067* (2013.01); *C07C 2603/32* (2017.05); *C09K 2211/1007* (2013.01); *C09K 2211/1014* (2013.01); *C09K 2211/1029* (2013.01); *C09K 2211/1044* (2013.01); *H01L 51/0096* (2013.01); *H01L 51/424* (2013.01); *H01L 51/44* (2013.01); *H01L 51/5056* (2013.01); *H01L 51/5072* (2013.01); *H01L 51/5096* (2013.01); *Y02E 10/549* (2013.01)

(58) Field of Classification Search
CPC . C09K 11/06; C09K 2211/00; C09K 2211/10; C09K 2211/1007; C09K 2211/1014; C09K 2211/1029; C09K 2211/1044; C07D 209/86; C07D 213/06; C07D 213/025; C07D 221/20; C07D 235/02; C07D 235/20; C07D 251/24; C07D 471/00; C07D 471/04; C07D 471/10; C07D 401/00; C07D 401/10; C07D 401/14; C07D 403/00; C07D 403/10; C07D 403/14; C07D 487/00; C07D 487/04; C07D 487/10; Y02E 10/549; C07C 2603/32; C07C 211/58; C07C 255/52; C07F 9/5329; H01L 51/0032; H01L 51/005; H01L 51/0052; H01L 51/0058; H01L 51/006; H01L 51/0061; H01L 51/0067; H01L 51/0072; H01L 51/008; H01L 51/0096; H01L 51/424; H01L 51/44; H01L 51/50; H01L 51/5012; H01L 51/5016; H01L 51/5056; H01L 51/5072; H01L 51/5096
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS 6,229,012 B1 * 5/2001 Hu ................. C07D 251/24
                                               544/180
9,209,413 B1 * 12/2015 Chen ................. H01L 51/0072
2006/0041126 A1 * 2/2006 Schafer ............. C07D 239/26
                                               544/242

FOREIGN PATENT DOCUMENTS

JP        2010024149 A  *  2/2010

OTHER PUBLICATIONS

Machine translation of JP2010-024149. (Year: 2010).*

* cited by examiner

*Primary Examiner* — Andrew K Bohaty
(74) *Attorney, Agent, or Firm* — Muncy, Geissler, Olds & Lowe, P.C.

(57) ABSTRACT

The present invention provides a series of spirally configured cis-stilbene/fluorene hybrid compounds and an optoelectronic device comprising the same. The compound comprises a seven-membered ring portion. The seven-membered ring portion is composed of a cis-stilbene fragment, and a tetrahedral coordination bridging atom fragment, wherein the cis-stilbene fragment has at least one substituent, the substituent is independently a substituted or unsubstituted triazine group, pyrimidine group or phenyl group. The compounds have glass transition temperatures ranged from 156° C. to 202° C., decomposition temperatures ranged from 419° C. to 509° C., reversible electron transport property, and balanced charges motilities. In addition, a variety of experimental data have proved that these spirally configured cis-stilbene/fluorene hybrid materials can indeed be used as a hole-blocking type electron-transporter for phosphorescent OLEDs.

5 Claims, 1 Drawing Sheet

(51) Int. Cl.
*H01L 51/00* (2006.01)
*C07D 235/02* (2006.01)
*C07D 403/14* (2006.01)
*C07D 401/14* (2006.01)
*C07C 255/52* (2006.01)
*C07F 9/53* (2006.01)
*C07C 211/58* (2006.01)
*C07D 209/86* (2006.01)
*C07D 213/06* (2006.01)
*C07D 235/20* (2006.01)
*C07D 251/24* (2006.01)
*C07D 471/04* (2006.01)
*C07D 487/04* (2006.01)
*C07F 5/02* (2006.01)
*C09K 11/02* (2006.01)
*C07D 221/20* (2006.01)
*C07D 471/10* (2006.01)
H01L 51/50 (2006.01)
H01L 51/44 (2006.01)
H01L 51/42 (2006.01)

SPIRALLY CONFIGURED CIS-STILBENE/FLUORENE HYBRID COMPOUNDS AND ORGANIC LIGHT EMITTING DEVICE COMPRISING THE SAME

CROSS REFERENCE TO RELATED APPLICATIONS

This patent application claims the benefit of U.S. Provisional Application No. 62/200,929, filed on Aug. 4, 2015, the content of which is hereby incorporated by reference in its entirety.

BACKGROUND OF THE INVENTION

Field of Invention

The present invention relates to the technology field of carrier transport and emitting materials, and more particularly to a series of spirally configured cis-stilbene/fluorene hybrid material as a hole-blocking type electron-transporters and emitters for OLEDs.

Related Art

It is well known that organic light emitting diode (OLED) was initially invented and proposed by Eastman Kodak Company through a vacuum evaporation method. Tang and VanSlyke of Kodak Company deposited an electron transport material such as $Alq_3$ on a transparent indium tin oxide (abbreviated as ITO) glass formed with an organic layer of aromatic diamine thereon, and subsequently completed the fabrication of an organic electroluminescent (EL) device after a metal electrode is vapor-deposited onto the $Alq_3$ layer. The organic EL device currently becomes a new generation lighting device or display because of high brightness, fast response speed, light weight, compactness, true color, no difference in viewing angles, without using any LCD backlight plates, and low power consumption.

Recently, some interlayers such as electron transport layer and hole transport layer are added between the cathode and the anode for increasing the current efficiency and power efficiency of the OLEDs. For example, an organic light emitting diode (OLED) 1' shown as FIG. 1 is designed to consist of: a cathode 11', an electron injection layer 13', a light emitting layer 14', a hole transport layer 16', and an anode 18'.

In device function concept, the light emitted by the OLED 1' is resulted from excitons produced by the recombination of electrons and holes in the light emitting layer 14'. However, according to theoretical speculation, the ratio of the excitons with singlet excited state and the excitons with triplet excited state is 3:1. So that, when a small molecular fluorescent material is used as the light-emitting layer 14' of the OLED 1', there are about 25% excitons being used in emitting light, and the rest of 75% excitons with triplet excited state are lost through non-luminescence mechanism. For this reason, the general fluorescent material performs a maximum quantum yield of 25% in limit which amounts to an external quantum efficiency of 5% in the device.

Moreover, researches further find that certain hole transport material can simultaneously perform electron confining ability, such as the material represented by following chemical formulas 1' and 2'. The chemical formula 1' represents the chemical structure of Tris(4-carbazoyl-9-ylphenyl) amine, which is called TCTA in abbreviation. The chemical formula 2' represents the chemical structure of N,N'-Di(1-naphthyl)-N,N'-diphenyl-(1,1'-biphenyl)-4,4'-diamine called NPB in abbreviation.

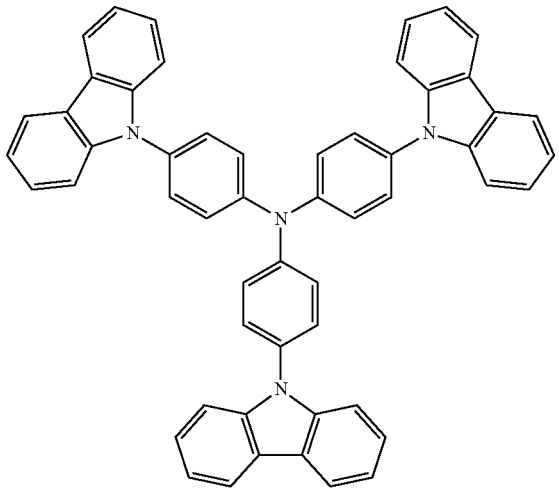

[chemical formula 1']

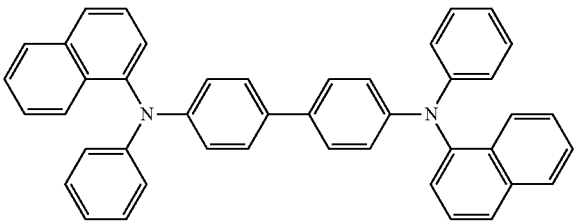

[chemical formula 2']

Recently, for effectively increasing the lighting performance of OLEDs, OLED manufactures and researchers have made great efforts to develop electron transport materials with hole blocking functionality, such as TmPyPb, TPBi, 3TPYMB, BmPyPb, and DPyPA represented by following chemical formula 3'-7', respectively. Wherein TmPyPb is the abbreviation of 3,3'-[5'-[3-(3-Pyridinyl)phenyl][1,1':3',1''-terphenyl]-3,3''-diyl]bispyridine, TPBi is the abbreviation of 1,3,5-Tris(1-phenyl-1H-benzimidazol-2-yl)benzene, 3TPYMB is the abbreviation of Tris(2,4,6-triMethyl-3-(pyridin-3-yl)phenyl)borane, BmPyPb is the abbreviation of 1,3-bis(3,5-dipyrid-3-yl-phenyl)benzene, and DPyPA is the abbreviation of 9,10-bis(3-(pyridin-3-yl)phenyl) anthracene.

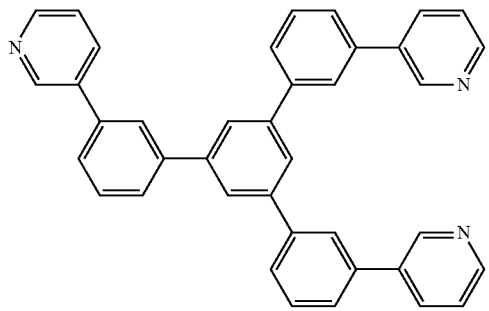

[chemical formula 3']

-continued

[chemical formula 4']

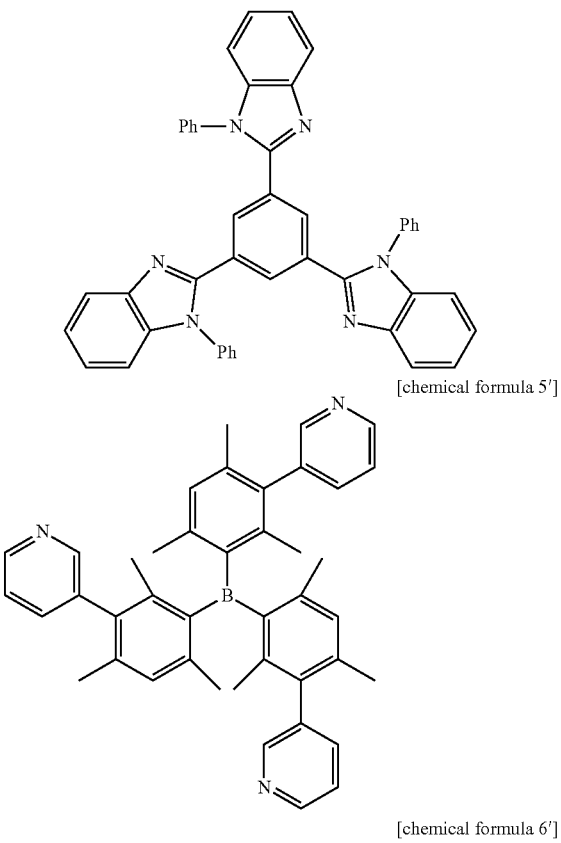

[chemical formula 5']

[chemical formula 6']

[chemical formula 7']

In spite of various electron transport materials with hole blocking functionality have been developed, the phosphorescence OLEDs applied with the said electron transport materials still cannot perform outstanding luminous efficiency and device lifetime. Accordingly, in view of the conventional or commercial electron transport materials with hole blocking functionality still including drawbacks, the inventor of the present application has made great efforts to make inventive research thereon and eventually provided a series of spirally configured cis-stilbene/fluorene hybrid materials bearing triazine, pyrimidine and phenyl subunits as hole-blocking type electron-transporters and emitters for OLED.

SUMMARY OF THE INVENTION

An aspect of the disclosure is to provide a series of spirally configured cis-stilbene/fluorene hybrid compounds and an optoelectronic device comprising the same. The compounds bear triazine, pyrimidine and phenyl subunits, and are spirally-configured cis-stilbene/fluorene derivatives having glass transition temperatures ranged from 156° C. to 202° C., decomposition temperatures ranged from 419° C. to 509° C., reversible electron transport property, and balanced charges motilities. In addition, these spirally configured cis-stilbene/fluorene hybrid compounds are shown to be capable of being used as hole-blocking type electron-transporters and emitting materials for OLEDs.

Therefore, one objective of the present invention is to provide a compound which comprises a seven-membered ring portion. The seven-membered ring portion is composed of a cis-stilbene fragment, and a tetrahedral coordination bridging atom fragment, wherein the cis-stilbene fragment has at least one substituent, the substituent is independently a substituted or unsubstituted triazine group, pyrimidine group or phenyl group.

Another objective of the present invention is to provide an optoelectronic device comprising a first electrode, an interlayer and a second electrode sequentially disposed on a substrate, wherein the interlayer has a compound. The compound comprises a seven-membered ring portion, and the seven-membered ring portion is composed of a cis-stilbene fragment, and a tetrahedral coordination bridging atom fragment, wherein the cis-stilbene fragment has at least one substituent, the substituent is independently a substituted or unsubstituted triazine group, pyrimidine group or phenyl group.

In one embodiment, the tetrahedral coordination bridging atom fragment is selected from the groups of general formulas I-1-1 to I-1-4.

(general formula I-1-1)

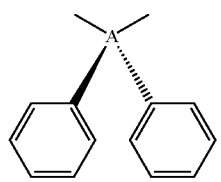
(general formula I-1-2)

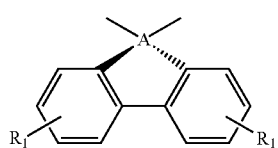
(general formula I-1-3)

(general formula I-1-4)

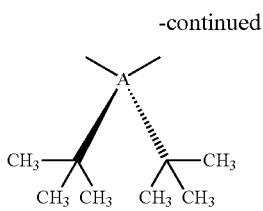

A is carbon atom or silicon atom, $R_1$ is a hydrogen atom, tert-butyl group or naphthyl group.

In one embodiment, the compound is applied in an organic light emitting device (OLED) for being as a hole-blocking material, an electron-transporting material and/or a light emitting material.

In one embodiment, the compound is represented by general formula I:

(general formula I)

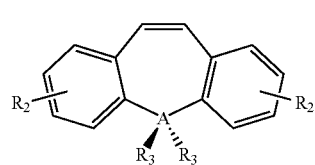

wherein $R_2$ is independently a triazine group, pyrimidine group or phenyl group optionally substituted by one or more radicals Y; when $R_2$ is a triazine group, radical Y is identical or different on each occurrence and is a hydrogen atom, cyano group, trifluoromethyl group, alkyl group, alkenyl group, aromatic ring group or heteroaromatic ring group optionally substituted by one or more radicals Y'; when $R_2$ is a pyrimidine group, radical Y is identical or different on each occurrence and is cyano group, trifluoromethyl group, alkyl group, alkenyl group, aromatic ring group or heteroaromatic ring group optionally substituted by one or more radicals Y'; when $R_2$ is phenyl group, radical Y is identical or different on each occurrence and is a hydrogen atom or triazine group optionally substituted by one or more radicals Y'; wherein radical Y' is identical or different on each occurrence and is a hydrogen atom, cyano group, diphenylamine group, aromatic ring group, heteroaromatic ring group, alkyl group or alkenyl group; and wherein $R_3$ is independently a methyl group, phenyl group, tert-butyl group or two of $R_3$ are linked by a single bond represented by general formula I-2, (general formula I-2)

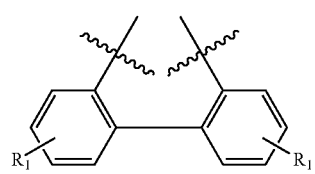

wherein $R_1$ is a hydrogen atom, tert-butyl group or naphthyl group.

In one embodiment, the aromatic ring group or heteroaromatic ring group in Y or Y' is independently a fused aryl group or heteroaryl group.

In one embodiment, the aromatic ring group or heteroaromatic ring group in Y is a phenyl group, 1-naphthyl group, 2-naphthyl group, thiophenyl group, pyrimidinyl group, pyrrolyl group, quinolinyl group, triazinyl group, pyridyl group or benzimidazolyl group.

In one embodiment, the aromatic ring or heteroaromatic ring group in Y' is an imidazolyl group, phenyl group, pyridyl group, 1H-pyrrolo[2,3-b]pyridine group or carbazolyl group.

In one embodiment, the alkyl group or alkenyl group in Y or Y' is independently a straight-chain alkyl group or alkenyl group, a branched alkyl group or alkenyl group, or a cyclic alkyl group or alkenyl group.

In one embodiment, $R_2$ is a triazine group which is selected from the group consisting of general formula II-1-1 to general formula II-1-19.

(general formula II-1-1)

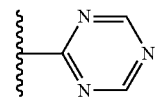

(general formula II-1-2)

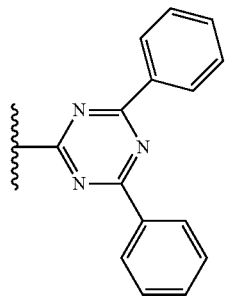

(general formula II-1-3)

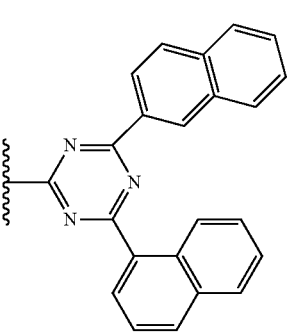

(general formula II-1-4)

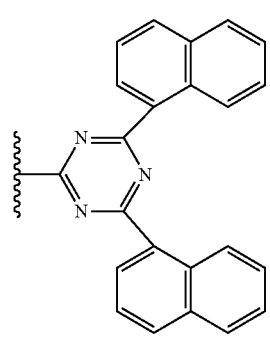

(general formula II-1-5)
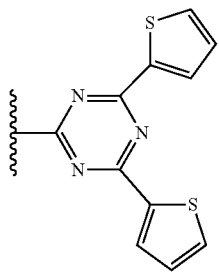
(general formula II-1-6)
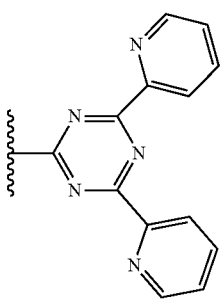
(general formula II-1-7)
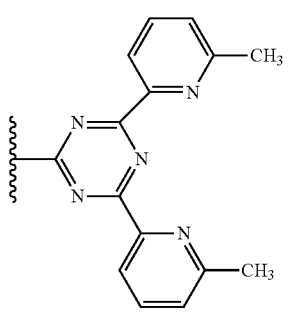
(general formula II-1-8)
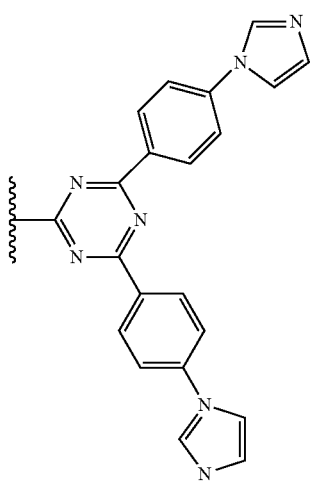
(general formula II-1-9)
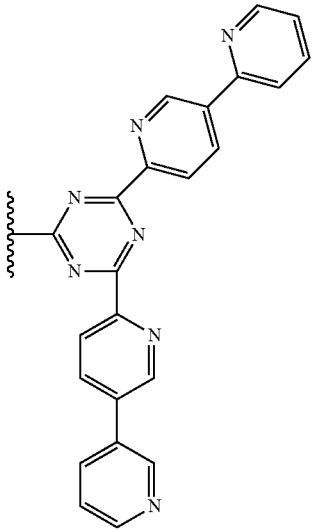
(general formula II-1-10)
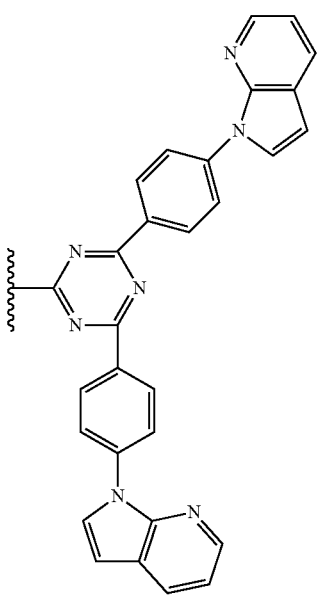
(general formula II-1-11)
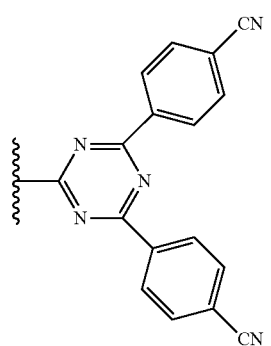

(general formula II-1-12)
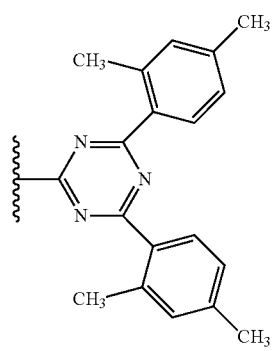
(general formula II-1-13)
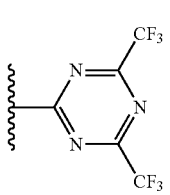
(general formula II-1-14)
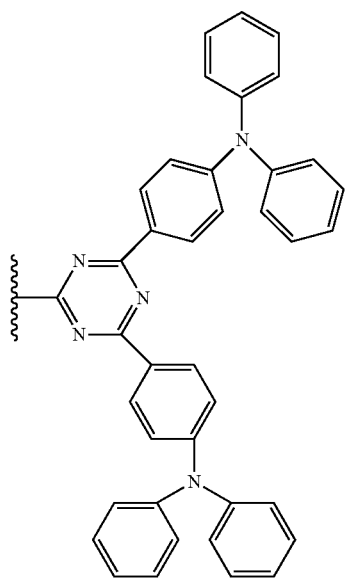
(general formula II-1-15)
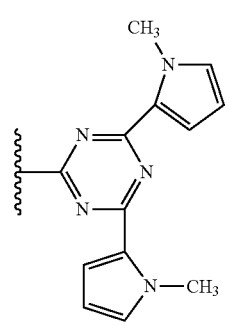
(general formula II-1-16)
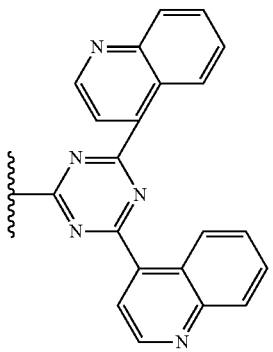
(general formula II-1-17)
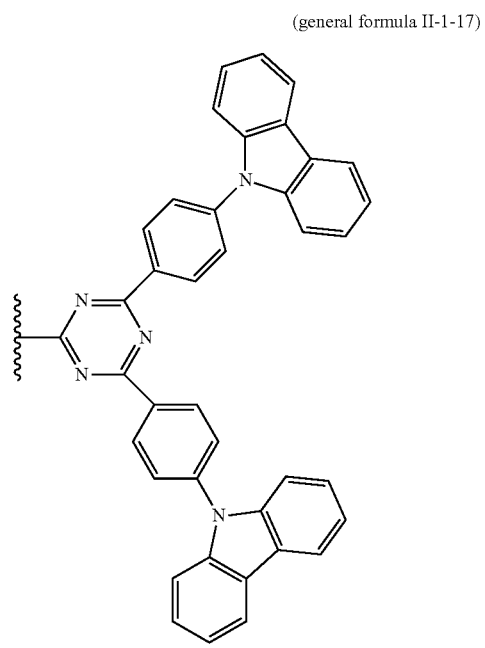
(general formula II-1-18)
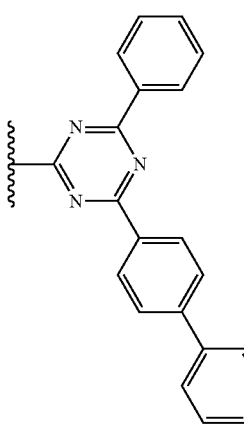

(general formula II-1-19)

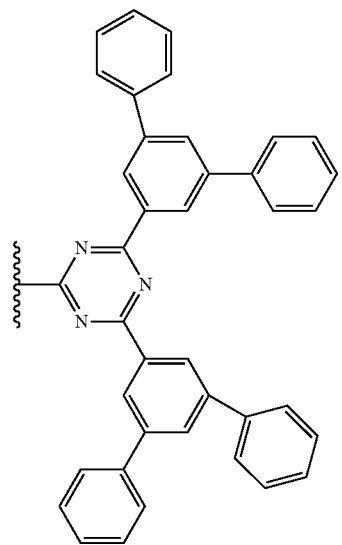

In one embodiment, $R_2$ is a pyrimidine group which is selected from the group consisting of general formula II-2-1 to formula II-2-10.

(general formula II-2-1)
(general formula II-2-2)
(general formula II-2-3)
(general formula II-2-4)
(general formula II-2-5)
(general formula II-2-6)

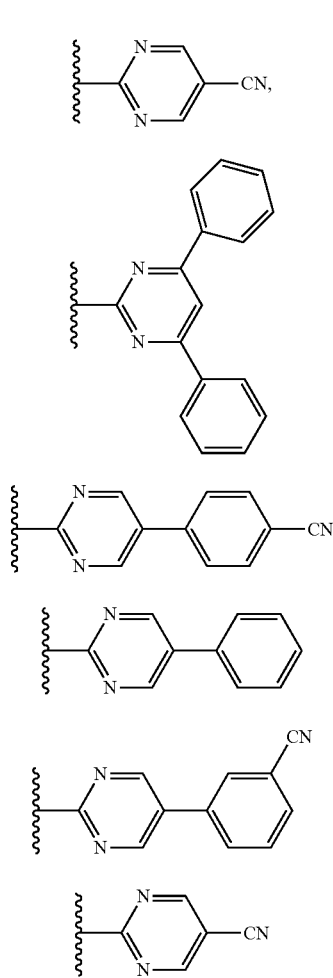

(general formula II-2-7)
(general formula II-2-8)
(general formula II-2-9)
(general formula II-2-10)

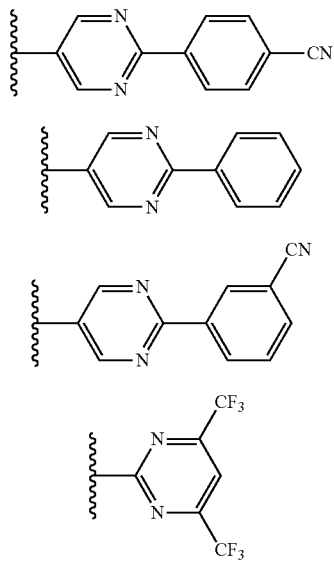

In one embodiment, $R_2$ is a phenyl group which is selected from the group consisting of general formula II-3-1 to general formula II-3-4.

(general formula II-3-1)
(general formula II-3-2)
(general formula II-3-3)
(general formula II-3-4)

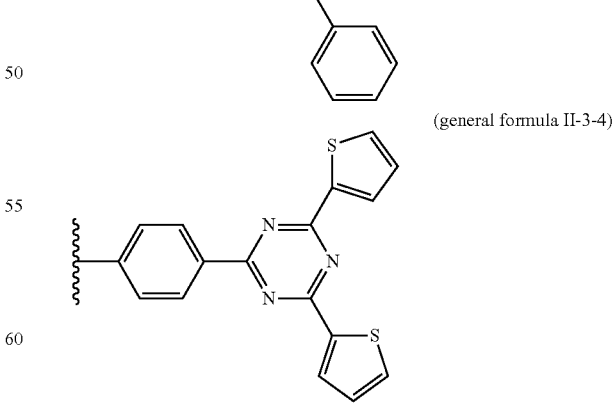

In one embodiment, the compound has glass transition temperatures (Tg) ranged from 156° C. to 202° C., decomposition temperatures (Td) ranged from 419° C. to 463° C., oxidation potentials ranged from 1.04 V to 1.16 V and redox potentials ranged from −1.75 V to −1.93 V.

In one embodiment, the optoelectronic device is an organic light emitting device (OLED), the interlayer is an electron transport layer, a hole blocking layer and/or a light emitting layer.

As mentioned above, as to the series of spirally configured cis-stilbene/fluorene hybrid compounds and the optoelectronic device comprising the same according to the disclosure, the compounds bear triazine, pyrimidine and phenyl subunits, and are spirally-configured cis-stilbene/fluorene derivatives. In addition, a variety of experimental data have proved that these spirally configured cis-stilbene/fluorene hybrid compounds can indeed be used as hole-blocking type electron-transporters and emitting materials for OLEDs. Moreover, the experimental data also reveal that the OLEDs using these spirally configured cis-stilbene/fluorene hybrid compounds can indeed be used as the hole-blocking type electron-transporters and are able to show excellent external quantum efficiency ($\eta_{ext}$), current efficiency ($\eta_c$), power efficiency ($\eta_p$), maximum luminance ($L_{max}$), and device lifetime better than those of phosphorescent OLEDs based on the conventional or commercial electron transport materials.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

Figure 1:
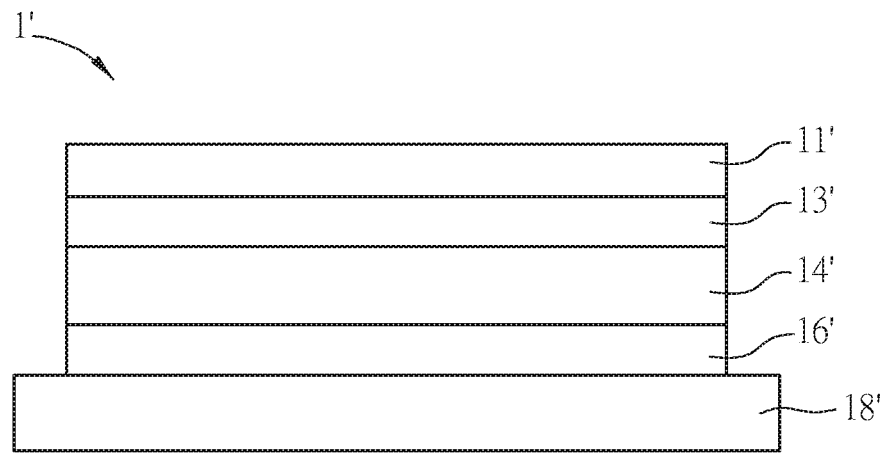
FIG. 1 is a schematic diagrams showing a conventional organic light emitting diode (OLED)

The embodiments of the invention will be apparent from the following detailed description, which proceeds with reference to the accompanying drawings, wherein the same references relate to the same elements.

The present invention provides a series of spirally configured cis-stilbene/fluorene hybrid compounds bearing triazine, pyrimidine and phenyl subunits for OLEDs. These spirally configured cis-stilbene/fluorene hybrid compounds, constructed by at least one cis-Stilbene based component and at least one fluorene based component, are spirally-configured cis-stilbene/fluorene derivatives having the functions to block holes. These spirally configured cis-stilbene/fluorene hybrid materials are mainly applied in OLEDs for being as an electron transport layer and/or a hole blocking layer; moreover, these spirally configured cis-stilbene/fluorene hybrid compounds can also be applied in a solar cell for being as a carrier transport layer.

According to one of the preferred embodiments of the present invention, a compound comprises a seven-membered ring portion. As described above, the compound can be applied in an organic light emitting device (OLED) for being as a hole-blocking material, an electron-transporting material and/or a light emitting material. The seven-membered ring portion is composed of a cis-stilbene fragment, and a tetrahedral coordination bridging atom fragment, wherein the cis-stilbene fragment has at least one substituent, the substituent is independently a substituted or unsubstituted triazine group, pyrimidine group or phenyl group. The tetrahedral coordination bridging atom fragment is selected from the groups of general formulas I-1-1 to I-1-4.

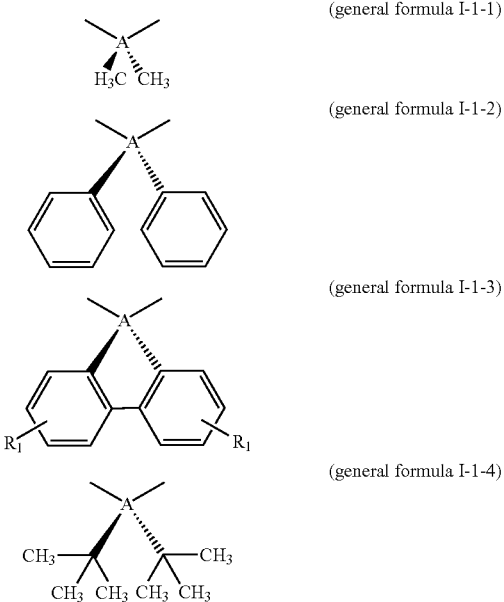

A is carbon atom or silicon atom, $R_1$ is a hydrogen atom, tert-butyl group or naphthyl group.

In one of the preferred embodiments of the present invention, the aforementioned spirally configured cis-stilbene/fluorene hybrid compound can be represented by general formula I:

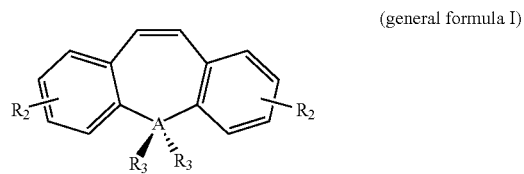

wherein $R_2$ is independently a triazine group, pyrimidine group or phenyl group optionally substituted by one or more radicals Y. When $R_2$ is a triazine group, radical Y is identical or different on each occurrence and is a hydrogen atom, cyano group, trifluoromethyl group, alkyl group, alkenyl group, aromatic ring group or heteroaromatic ring group optionally substituted by one or more radicals Y'. When $R_2$ is a pyrimidine group, radical Y is identical or different on each occurrence and is cyano group, trifluoromethyl group, alkyl group, alkenyl group, aromatic ring group or heteroaromatic ring group optionally substituted by one or more radicals Y'. When $R_2$ is phenyl group, radical Y is identical or different on each occurrence and is a hydrogen atom or triazine group optionally substituted by one or more radicals Y'. Said radical Y' is identical or different on each occurrence and is a hydrogen atom, cyano group, diphenylamine group, aromatic ring group, heteroaromatic ring group, alkyl group or alkenyl group. $R_3$ is independently a methyl group, phenyl group, tert-butyl group, or two of $R_3$ are linked by a single bond represented by general formula I-2,

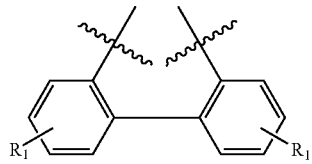
(general formula I-2)

wherein $R_1$ is a hydrogen atom, tert-butyl group or naphthyl group.

In addition, the aromatic ring group or heteroaromatic ring group in Y or Y' is independently a fused aryl group or heteroaryl group. For example, the aromatic ring group or heteroaromatic ring group in Y can be a phenyl group, 1-naphthyl group, 2-naphthyl group, thiophenyl group, pyrimidinyl group, pyrrolyl group, quinolinyl group, triazinyl group, pyridyl group or benzimidazolyl group, and the aromatic ring or heteroaromatic ring group in Y' can be an imidazolyl group, phenyl group, pyridyl group, 1H-pyrrolo[2,3-b]pyridine group or carbazolyl group.

The alkyl group or alkenyl group in Y or Y' is independently a straight-chain alkyl group or alkenyl group, a branched alkyl group or alkenyl group, or a cyclic alkyl group or alkenyl group.

In detail, if $R_2$ is a triazine group, it can be any one of the radical which is selected from the group consisting of general formula II-1-1 to general formula II-1-19.

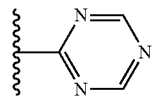
(general formula II-1-1)

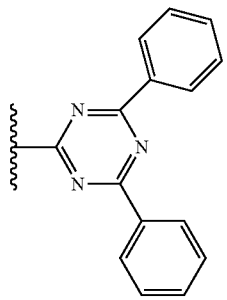
(general formula II-1-2)

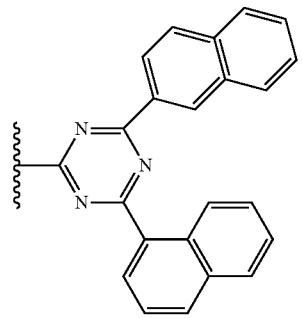
(general formula II-1-3)

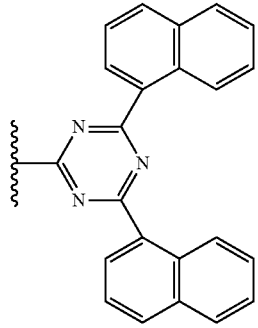
(general formula II-1-4)

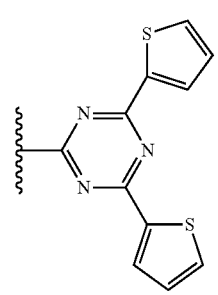
(general formula II-1-5)

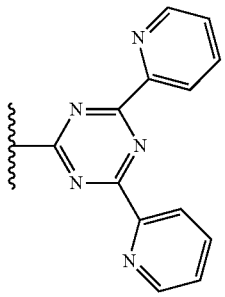
(general formula II-1-6)

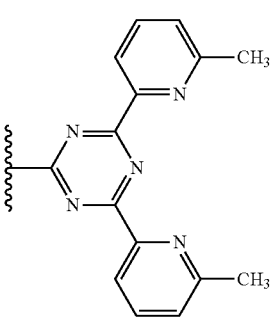
(general formula II-1-7)

(general formula II-1-8)
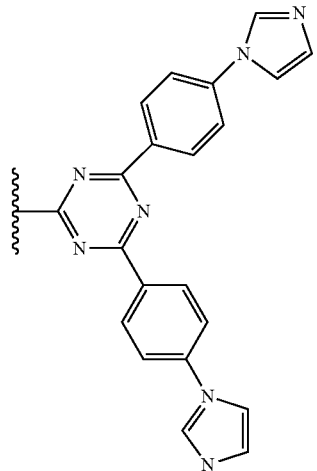
(general formula II-1-9)
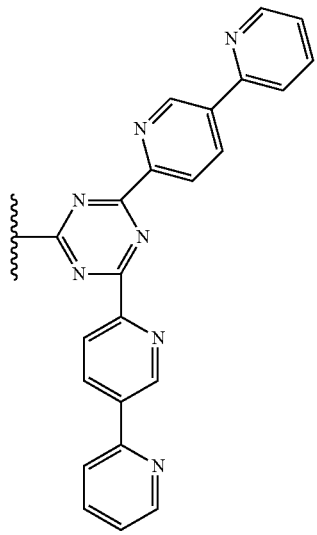
(general formula II-1-10)
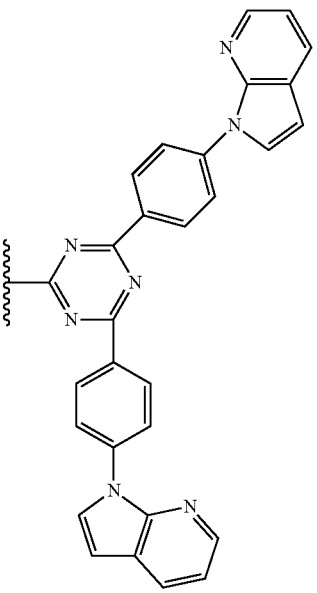
(general formula II-1-11)
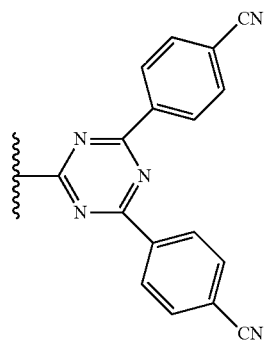
(general formula II-1-12)
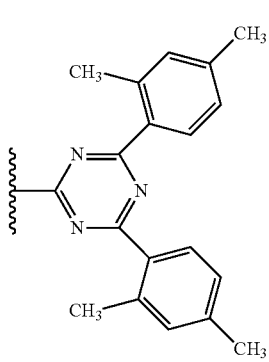
(general formula II-1-13)
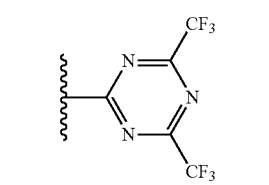
(general formula II-1-14)
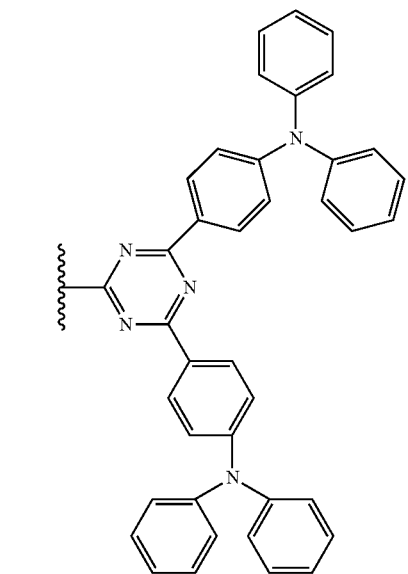

(general formula II-1-15)
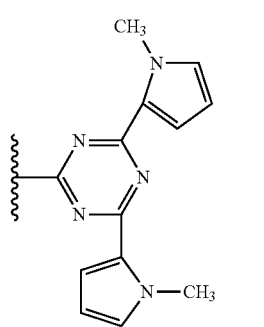
(general formula II-1-16)
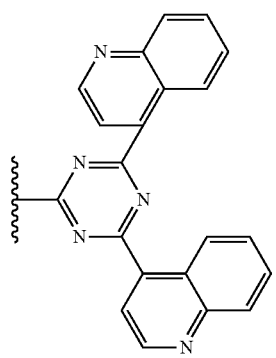
(general formula II-1-17)
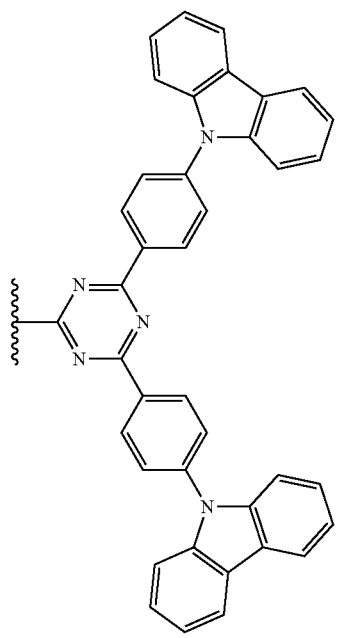
(general formula II-1-18)
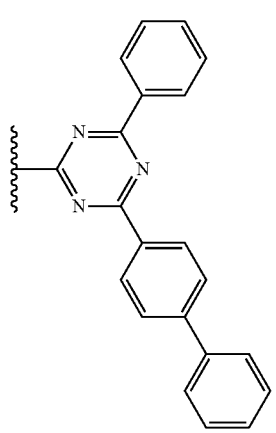
(general formula II-1-19)
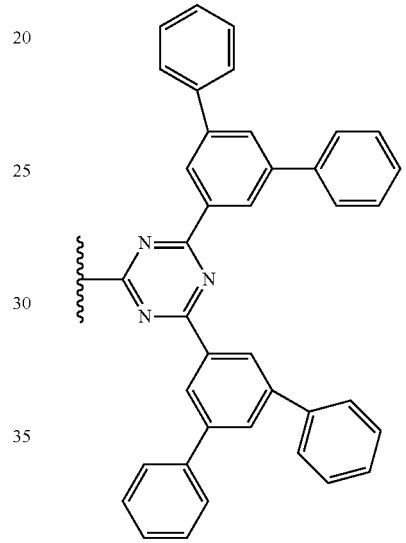
When $R_2$ is a pyrimidine group, it then can be selected from the group consisting of general formula II-2-1 to formula II-2-10.
(general formula II-2-1)
(general formula II-2-2)
(general formula II-2-3)
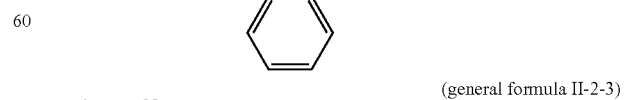

(general formula II-2-4)
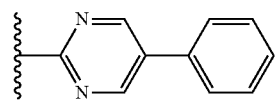

(general formula II-2-5)
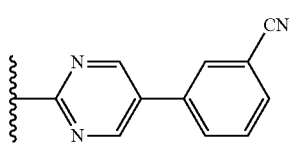

(general formula II-2-6)
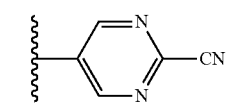

(general formula II-2-7)
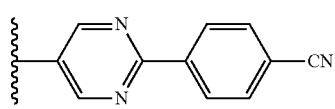

(general formula II-2-8)
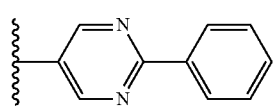

(general formula II-2-9)
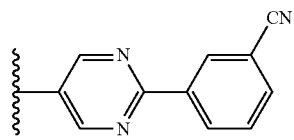

(general formula II-2-10)
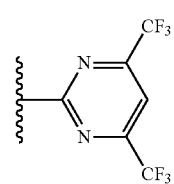

In addition, when $R_2$ is a phenyl group, it can be selected from the group consisting of general formula II-3-1 to general formula II-3-4.

(general formula II-3-1)
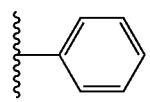

(general formula II-3-2)
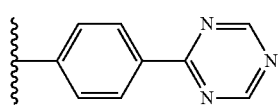

(general formula II-3-3)
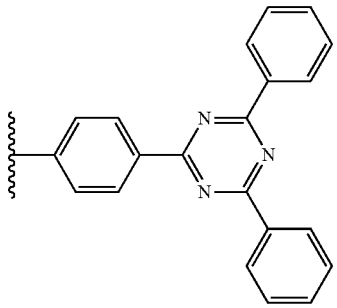

(general formula II-3-4)
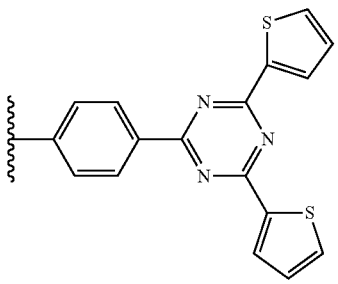

To manufacture the said spirally configured cis-stilbene/fluorene hybrid materials of the present invention, a key intermediate product needs to be firstly fabricated by using following steps:

(1) dissolving 30 mM 2-bromobiphenyl of 5.2 mL in 100 mL of anhydrous tetrahydrofuran (THF);

(2) placing the solution obtained from the step (1) in an environment of −78° C. for standing;

(3) taking 12 mL of n-butyllithium in hexanes solution (30 mM) from a n-butyllithium solution 2.5 M in hexanes, and then adding the 12 mL n-butyllithium hexanes solution dropwise into the solution obtained from the step (2) and stirring for 30 min (4) dissolving 20 mM 3,7-dibromo-dibenzosuberenone of 7.28 g in 60 mL of anhydrous THF;

(5) adding the solution obtained from step (4) to the reaction mixture in step (3) dropwise;

(6) adding 10 mL of saturated aqueous sodium bicarbonate solution into the product obtained from the step (5) for executing a quenching reaction, and then remove the THF by rotary evaporation;

(7) treating the product obtained from the step (6) with a extracting process by using dichloromethane, and then obtaining an extract liquid extract;

(8) adding 5 g magnesium sulfate into the extract liquid extract, and then treat a drying process and a filtering process to the liquid extract sequentially; and (9) using a rotary evaporating process to the product obtained from the step (8), so as to obtain a an intermediate product.

Furthermore, the following steps can be used for making another intermediate product of clear crystalline material.

(10) dissolving the intermediate product from step (9) in 60 m acetic acid;

(11) adding 1 mL of concentrated hydrochloric acid (12 N) into the solution obtained from the step (10);

(12) letting the solution mixture obtained from the step (11) to react for 2 hours at 120° C. by using a reflux device;

(13) cooling the temperature of the product obtained from the step (12) down to 0° C.;

(14) adding 60 mL hexane into the product obtained from the step (13);

(15) using a Buchner funnel to treat the product obtained from the step (14) with a filtering process, so as to obtain a precipitate;

(16) using hexane to wash the precipitate for 3 times, so as to obtain a solid material;

(17) using dichloromethane/hexane to treat the solid with a recrystallization process for obtaining a clear crystal solid, wherein the clear crystal solid is presented by following chemical formula 1.

[chemical formula 1]

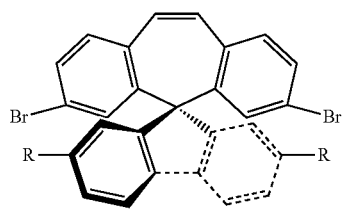

Furthermore, various exemplary embodiments for the spirally configured cis-stilbene/fluorene hybrid materials of the present invention can be fabricated by treating certain chemical reaction method to the key intermediate product of clear crystalline materials represented by the chemical formula 1, such as Suzuki coupling, Hartwig reaction and Rosemund-VonBarann method. Therefore, the exemplary embodiments of these spirally configured cis-stilbene/fluorene hybrid compounds are represented by following chemical formula II, chemical formula III, chemical formula IV, chemical formula V, chemical formula VI.

[chemical formula II]

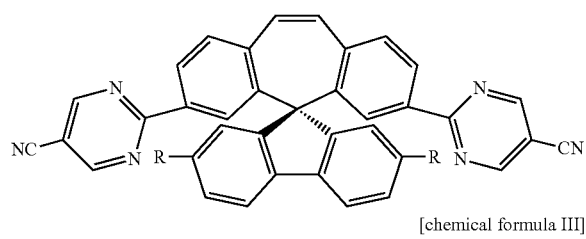

[chemical formula III]

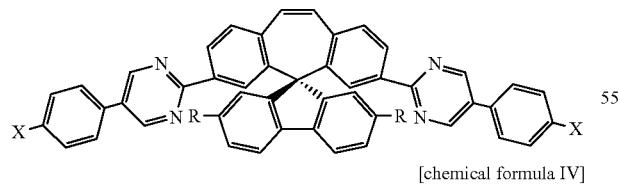

[chemical formula IV]

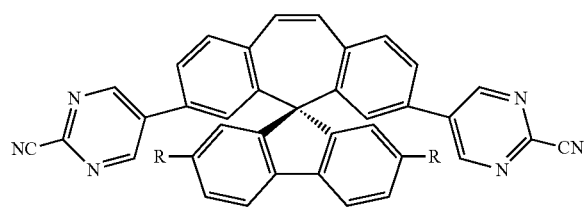

[chemical formula V]

[chemical formula VI]

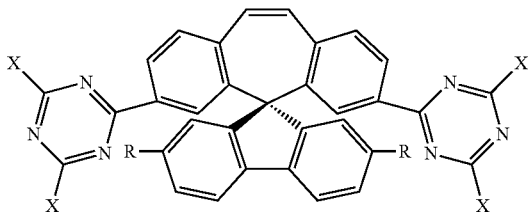

In the above-presented chemical formulas, R can be hydrogen group or tert-butyl group, and X is hydrogen, phenyl or C—N group.

Moreover, the data of glass transition temperature ($T_g$), decomposition temperature ($T_d$), the longest peak wavelength value of absorption spectrum ($\lambda_{max}$), and the longest peak wavelength value of photoluminescence spectrum (PL_$\lambda_{max}$) of the aforesaid compounds are measured and recorded in the following Table (1). From the Table (1), it is able to know that these spirally configured cis-stilbene/fluorene hybrid materials proposed by the present invention have glass transition temperatures ($T_g$) ranged from 156° C. to 202° C. and decomposition temperatures ($T_d$) ranged from 419° C. to 509° C. That means these spirally configured cis-stilbene/fluorene hybrid materials possess excellent thermal stability, and are not easy to decompose under high voltage and high current density operation conditions.

TABLE (1)

| Group | $T_g$ (° C.) | $T_d$ (° C.) | $\lambda_{max}$ (nm) | PL$\lambda_{max}$ (nm) |
|---|---|---|---|---|
| Embodiment 1 (CNN2SN2CN) | 164 | 425 | 372 | 435, 455 |
| Embodiment 2 (ΦN2SN2Φ) | 169 | 447 | 369 | 425, 450 |
| Embodiment 3 (CN'N2SN2CN') | 156 | 419 | 375 | 437, 460 |
| Embodiment 4 (Φ'N2SN2Φ') | 167 | 442 | 367 | 423, 448 |
| Embodiment 5 (N3SN3) | 202 | 509 | 371 | 430, 456 |

Moreover, the oxidation potential and the redox potential of the embodiments 1-5 of these spirally configured cis-stilbene/fluorene hybrid materials can be measured by way of cyclic voltammetry (CV); therefore, the highest occupied molecular orbital energy level ($E_{HOMO}$) and lowest unoccupied molecular orbital energy level ($E_{LUMO}$) of the embodiments 1-5 of these spirally configured cis-stilbene/fluorene hybrid materials can also be calculated based on the measured oxidation potential ($E_{1/2}^{ox}$) and the redox potential ($E_{1/2}^{red}$). With reference to following Table (2), $E_{1/2}^{ox}$, $E_{1/2}^{red}$, $E_{HOMO}$, and $E_{LUMO}$ of the spirally configured cis-stilbene/fluorene hybrid materials are recorded. From the Table (2), the persons skilled in OLED material art are able to know that these spirally configured cis-stilbene/fluorene hybrid materials proposed by the present invention have the $E_{HOMO}$ ranged from 6.1 eV to 6.4 eV and the $E_{LUMO}$ ranged from 3.2 eV to 3.4 eV. Moreover, these spirally configured cis-stilbene/fluorene hybrid materials also have the oxidation potentials ranged from 1.04 V to 1.16 V and the redox potentials ranged from −1.75 V to −1.93 V.

TABLE (2)

| Group | $E_{1/2}^{ox}$ (V) | $E_{1/2}^{red}$ (V) | $E_g$ (eV) | $E_{HOMO}$ (eV) | $E_{LUMO}$ (eV) |
| --- | --- | --- | --- | --- | --- |
| Embodiment 1 ($CNN_2SN_2CN$) | 1.15 | −1.75 | 3.00 | 6.2 | 3.2 |
| Embodiment 2 ($\Phi N_2SN_2\Phi$) | 1.05 | −1.91 | 2.99 | 6.2 | 3.2 |
| Embodiment 3 ($CN'N_2SN_2CN'$) | 1.16 | −1.73 | 2.94 | 6.3 | 3.3 |
| Embodiment 4 ($\Phi'N_2SN_2\Phi'$) | 1.04 | −1.93 | 2.99 | 6.1 | 3.2 |
| Embodiment 5 ($N_3SN_3$) | 1.08 | −1.88 | 3.08 | 6.4 | 3.4 |

In order to prove that these proposed spirally configured cis-stilbene/fluorene hybrid materials can indeed be applied in OLEDs for being as a hole-blocking type electron transport layer, a plurality of OLED devices for control groups and experiment groups have been designed and manufactured, wherein the constituting layers for the OLED devices are integrated in the following Table (3).

In the Table (3), 1,4,5,8,9,11-Hexaazatriphenylene-hexacarbonitrile (HATCN) is used as the HIL; 4,4'-Cyclohexylidenebis [N,N-bis(4-methylphenyl)benzenamine] (TAPC) is used as the HT01. BmPyPb is the abbreviation of 1,3-bis (3,5-dipyrid-3-yl-phenyl)benzene, DPyPA is the abbreviation of 9,10-bis(3-(pyridin-3-yl)phenyl)anthracene, and TPBi is the abbreviation of 1,3,5-Tris(1-phenyl-1H-benzimidazol-2-yl)benzene. In addition, ET01 is represented by following chemical formula 2″; and the green phosphorescent dopant is $Ir(ppy)_3$ along with 11-(4,6-diphenyl-1,3,5-triazin-2-yl)-12-phenyl-11,12-dihydroindolo[2,3-a]carbazole as the host which is represented by the following chemical formula (V).

[chemical formula 2″]

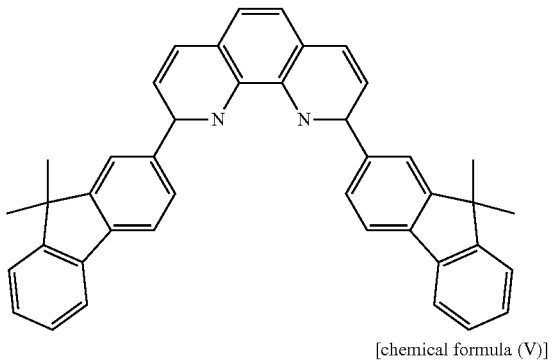

[chemical formula (V)]

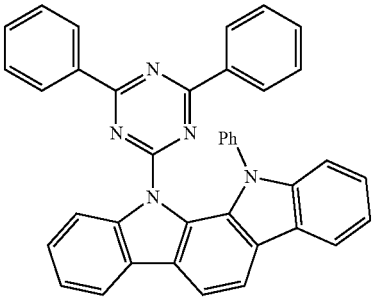

TABLE (3)

| Device Group | Substrate | bottom electrode | electron transport layer | hole blocking layer | Light emitting layer | Hole transport layer | top electrode |
| --- | --- | --- | --- | --- | --- | --- | --- |
| Experiment 1a | Al | LiF | $CNN_2SN_2CN$ | $CNN_2SN_2CN$ | green phosphorescent | TAPC | HIL/ITO |
| Experiment 1b | Al | LiF | $\Phi N_2SN_2\Phi$ | $\Phi N_2SN_2\Phi$ | green phosphorescent | TAPC | HIL/ITO |
| Experiment 2a | Al | LiF | $CN'N_2SN_2CN'$ | $CN'N_2SN_2CN'$ | green phosphorescent | TAPC | HIL/ITO |
| Experiment 2b | Al | LiF | $\Phi'N_2SN_2\Phi'$ | $\Phi'N_2SN_2\Phi'$ | green phosphorescent | TAPC | HIL/ITO |
| Experiment 3a | Al | LiF | $N_3SN_3$ | $N_3SN_3$ | green phosphorescent | TAPC | HIL/ITO |
| Control 1A | Al | LiF | BmPyPb | BmPyPb | green phosphorescent | TAPC | HIL/ITO |
| Control 1B | Al | LiF | DPyPA | DPyPA | green phosphorescent | TAPC | HIL/ITO |
| Control 1C | Al | LiF | TPBi | TPBi | green phosphorescent | TAPC | HIL/ITO |
| Experiment 4 | Al | LiF | $CN'N_2SN_2CN'$ | $CN'N_2SN_2CN'$ | green phosphorescent | NPB/HT01 | HIL/ITO |
| Experiment 5 | Al | LiF | $N_3SN_3$ | $N_3SN_3$ | green phosphorescent | NPB/HT01 | HIL/ITO |
| Control 2 | Al | LiF | BmPyPb | BmPyPb | green phosphorescent | NPB/HT01 | HIL/ITO |
| Control 3 | Al | LiF | ET01 | ET01 | green phosphorescent | NPB/HT01 | HIL/ITO |

It is able to know that the materials of TPBi, DPyPA, BmPyPb, and ET01 recorded in the Table (3) are also used as OLED device's electron transport layers. Continuously, the turn-on voltage ($V_{on}$), the external quantum efficiency ($\eta_{ext}$), the current efficiency ($\eta_c$), the power efficiency ($\eta_p$), and the maximum luminance ($L_{max}$) of the OLED devices have been measured and recorded in the following Table (4).

TABLE (4)

| Device Group | $\lambda_{max}$ (nm) | Von (V) | $\eta_{ext}$ (%) | $\eta_c/\eta_p$ (%) | $L_{max}$ (cd/m$_2$) |
|---|---|---|---|---|---|
| Experiment 1a | 516 | 2.3 | 14.4 | 52.5/65.7 | 143,500 |
| Experiment 1b | 516 | 2.2 | 13.3 | 51.2/45.5 | 92,835 |
| Experiment 2a | 516 | 2.1 | 13.5 | 52.0/61.5 | 139,800 |
| Experiment 2b | 516 | 2.3 | 13.0 | 47.4/63.6 | 96,120 |
| Experiment 3a | 516 | 2.3 | 14.0 | 50.4/37.2 | 122,000 |
| Control 1A | 516 | 2.5 | 6.3 | 22.8/18.0 | 142,100 |
| Control 1B | 516 | 3.0 | 10.2 | 37.8/24.0 | 40,700 |
| Control 1C | 516 | 3.0 | 6.9 | 24.7/22.0 | 37,640 |
| Experiment 4 | 516 | 5.5 | 11.3 | 42.1/24.1 | 74,580 |
| Experiment 5 | 516 | 4.8 | 11.9 | 39.5/24.7 | 41,200 |
| Control 2 | 516 | 4.5 | 10.8 | 36.8/25.7 | 42,150 |
| Control 3 | 516 | 5.5 | 7.84 | 27.6/15.8 | 17,700 |

With reference to the measured data of the green phosphorescent OLED devices in the Table (4), one can find that the OLED devices using single hole transport layer of Experiment 1a-b, Experiment 2a-b and Experiment 3a show excellent $\eta_{ext}$, $\eta_c$, $\eta_p$, and $L_{max}$ and are much superior to the OLED devices using single hole transport layer of Control 1A, Control 1B, and Control 1C. Among them, experiments 1a (CNN$_2$SN$_2$CN), 2b (CN'N$_2$SN$_2$CN'), and 3a (N$_3$SN$_3$) show the best results, where the $\eta_{ext}$ are in a range of 13.5-14.4%, $\eta_c$ are in a range of 50.4-52.5 cd/A, $\eta_p$ are in a range of 61.5-65.7 lm/w, and $L_{max}$ are in a range of 122,000-143,500 cd/m$^2$.

In addition, the measured data also reveal that the OLED devices using single hole transport layer of Experiment 1a-b, Experiment 2a-b and Experiment 3a show excellent $\eta_{ext}$, $\eta_c$, $\eta_p$, and $L_{max}$ and are superior to the OLED devices using complex (i.e., double) hole transport layer of Control 2 and Control 3. Moreover, the commercial OLED device using complex (double) hole transport layer of Experiment 4 (CN'N$_2$SN$_2$CN') also shows excellent $\eta_{ext}$, $\eta_c$, $\eta_p$, and $L_{max}$, which is superior to the OLED devices using complex (i.e., double) hole transport layer of Control 2 and Control 3.

Furthermore, device life time evaluation test for the green phosphorescent OLEDs have also been completed based on a starting luminance of 10,000 cd/cm$^2$. Life time evaluation test results reveal that the decay half lifetimes (LT$_{50}$) of the green phosphorescent OLED for Experiment 4 and 5 are 13,000 and 13,740 hours. In addition, the decay half lifetime (LT$_{50}$) for the green phosphorescent OLEDs of Control 1A and Control 3 are respectively measured as 1,000 hours and 13,500 hours. Moreover, after replacing the BmPyPb in the green phosphorescent OLEDs of Control 1A by the TmPyPb, the green phosphorescent OLEDs having the TmPyPb material is measured with the LT$_{50}$ of only 210 hours.

Therefore, through above descriptions, these spirally configured cis-stilbene/fluorene hybrid materials for OLEDs proposed by the present invention have been introduced completely and clearly; in summary, the present invention includes the advantages of:

(1) The spirally configured cis-stilbene/fluorene hybrid materials are spirally-configured cis-stilbene/fluorene derivatives bearing pyrimidine and triazine substituents having glass transition temperatures ranged from 156° C. to 202° C., decomposition temperatures ranged from 419° C. to 509° C., reversible electron transport property, and balanced charges motilities.

(2) Moreover, a variety of experimental data have proved that these spirally configured cis-stilbene/fluorene hybrid materials can indeed be used as a hole-blocking type electron-transporter for OLEDs; moreover, the experimental data also reveal that the OLEDs using these spirally configured cis-stilbene/fluorene hybrid materials can indeed be used as the hole-blocking type electron-transporter are able to show excellent external quantum efficiency ($\eta_{ext}$), current efficiency ($\eta_c$), power efficiency ($\eta_p$), maximum luminance ($L_{max}$), and device lifetime performances better than the conventional or commercial OLEDs.

Figure 2:
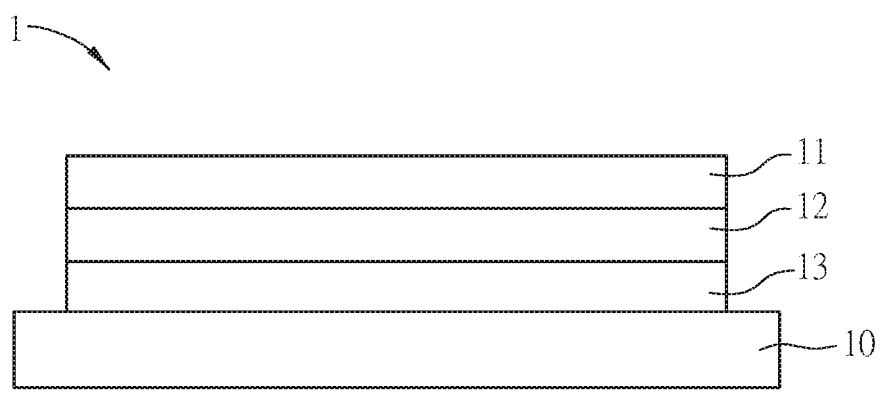
FIG. 2 is a schematic diagram of the optoelectronic device according to a preferred embodiment of the present invention.

The present invention also provides another preferred embodiment which is an optoelectronic device. As shown in FIG. 2, the optoelectronic device 1 comprises a first electrode 11, an interlayer 12 and a second electrode 13 sequentially disposed on a substrate 10. The interlayer has a compound substantially the same as described in the above-mentioned preferred embodiment of the present application. The compound comprises a seven-membered ring portion, and the seven-membered ring portion is composed of a cis-stilbene fragment, and a tetrahedral coordination bridging atom fragment, wherein the cis-stilbene fragment has at least one substituent, the substituent is independently a substituted or unsubstituted triazine group, pyrimidine group or phenyl group. The detail of the compounds, such as the feasible preferred substituents and electrical characteristics, can refer to the previous embodiments, and they are not repeated here.

In addition, the optoelectronic device 1 is an organic light emitting device (OLED), the interlayer 12 is an electron transport layer, a hole blocking layer and/or a light emitting layer. Moreover, the optoelectronic device 1 of the present preferred embodiment can be applied to an organic light emitting device, an organic solar cell device, an organic thin film transistor, an organic photodetector, a flat panel display, a computer monitor, a television, a billboard, a light for interior or exterior illumination, a light for interior or exterior signaling, a heads up display, a fully transparent display, a flexible display, a laser printer, a telephone, a cell phone, a tablet computer, a laptop computer, a digital camera, a camcorder, a viewfinder, a micro-display, a vehicle, a large area wall, a theater or stadium screen, or a sign.

The features of the spirally configured cis-stilbene/fluorene hybrid compounds and the optoelectronic devices according to the above embodiments will become more fully understood by the person who skilled in the art from the following experimental examples which further illustrate the physical and chemical properties thereof.

Example A

Synthesis of Intermediate B

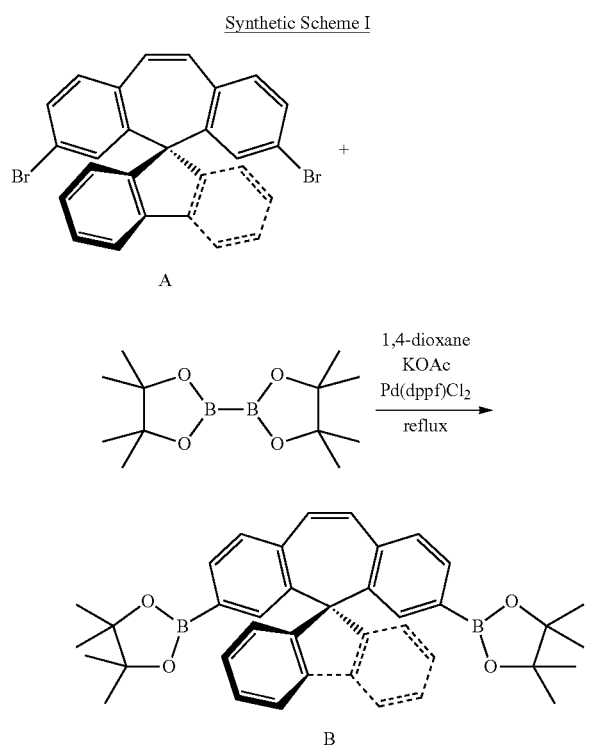

Synthetic Scheme I

According to Synthetic Scheme I, intermediate A (99%) 5 g (1 eq, 10 mmol), bis(pinacolato)diboron 5.587 g (2.2 eq, 22 mmol), Potassium acetate 5.899 g (6 eq, 60 mmol) and Pd(dppf)Cl$_2$ 146 mg(0.02 eq, 0.2 mmol) were dissolved in 1,4-dioxane 200 mL and remove the oxygen in −78° C., followed by being warmed to room temperature and the whole solution was refluxed for 24 hours. The reaction mixture was extracted with water and 150 mL of dichloromethane (three times) organic layer was separated and was dried with MgSO$_4$. The crude residue was purified by column chromatography on silica gel (CH2Cl2/hexanes, 1/1), followed by a process of evaporation of organic layer after filtration and then washed by 100 mL of methanol. After recrystallization with CH$_2$Cl$_2$/hexanes, 4.685 g of the product B was obtained with (yield: 79%). Spectral data as follow: Tm: 207° C. (DSC); M.W.: 594.35; $^1$H NMR (400 MHz, CDCl3) δ 7.98 (d, J=7.8, 2H), 7.73 (d, J=7.6, 2H), 7.59 (dd, J=7.5, 1.1, 2H) 7.39 (s, 2H), 7.35 (t, J=7.6, 2H), 7.23 (td, J=7.6, 1.2, 2H), 7.01 (s, 2H), 1.19 (s, 24H); $^{13}$C NMR (100 MHz, CDCl$_3$) δ 152.4, 141.3, 139.1, 138.8, 135.4, 134.3, 133.3, 131.3, 127.7, 127.1, 127.1, 120.2, 83.4, 66.0, 24.7; MS (EI, 20 eV) 594.3 (M+, 68); TLC R$_f$ 0.35 (acetone/hexanes, 1/1); High Resolution-MS calcd for C$_{39}$H$_{40}$B$_2$O$_4$: 594.3113. found: 594.3120.

Example B1

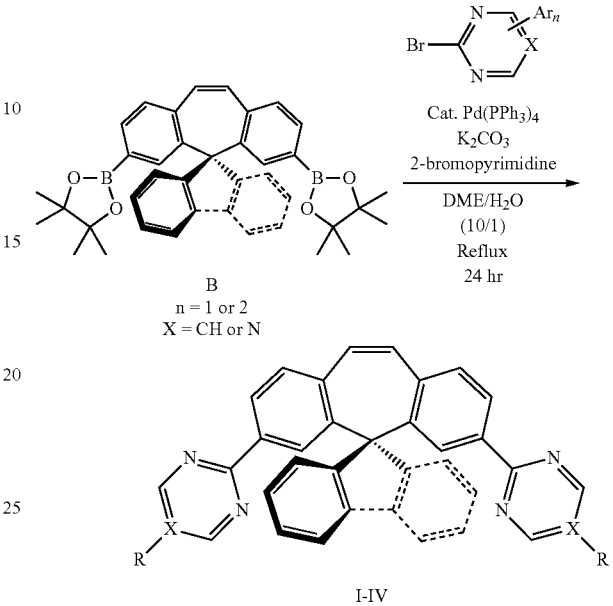

Synthetic Scheme IIA

According to Synthetic Scheme IIA, intermediate B (99%) 1.783 g (1 eq, 3 mmol), 2-bromopyrimidine (98%) 1.24 g (2.6 eq, 7.8 mmol), Potassium carbonate 1.658 (4 eq, 12 mmol), Pd(PPh$_3$)$_4$ 173 mg (0.05 eq, 0.15 mmol) was dissolved in DME and water (10:1) 110 mL under nitrogen gas and remove the oxygen in −78° C. The whole solution was refluxed for 24 hours. The reaction mixture was extracted with water and 50 mL of dichloromethane (three times) organic layer was separated and was dried with MgSO$_4$. The crude residue was purified by column chromatography on silica gel (EtOAc/dichloromethane/hexane, 1/15/15). The combined organic layers were dried (MgSO$_4$), filtered, and evaporated. The crude solid was re-crystallized from CH$_2$Cl$_2$/n-hexane to afford 1211 mg of pure compound I. Spectral data as follow: T$_m$: 329° C., T$_g$: 147° C., T$_d$: 383° C. (DSC); M.W.: 498.58; $^1$H NMR (400 MHz, CDCl$_3$) δ 8.61 (d, J=4.8, 4H), 8.25 (dd, J=8.0, 1.7, 2H), 8.17 (d, J=1.6, 2H), 8.07 (d, J=7.8, 2H), 7.77 (d, J=7.6, 2H), 7.50 (d, J=8.0, 2H), 7.41 (td, 7.5, 1.0, 2H), 7.31 (td, J=7.6, 1.1, 2H), 7.11 (s, 2H), 7.02 (t, J=4.8, 2H); $^{13}$C NMR (100 MHz, CDCl$_3$) δ 164.3, 157.0, 152.6, 142.2, 139.1, 138.6, 137.5, 133.9, 132.7, 129.2, 128.0, 127.5, 127.0, 126.9, 120.4, 118.7, 66.3; TLC R$_f$ 0.27 (EtOAc/dichloromethane/hexane, 1/15/15); High Resolution-MS calcd for C$_{35}$H$_{23}$N$_4$: 499.1917. found: 499.1926; Anal. Calcd for C$_{35}$H$_{22}$N$_4$: C, 84.32; H, 4.45; N, 11.24. Found: C, 83.961; H, 4.28; N, 11.206.

Example B2

According to Synthetic Scheme IIA, intermediate B (99%) 2.377 g (1 eq, 4 mmol), 2-bromo-5-cyano-pyrimidine (98%) 1.24 g (2.2 eq, 8.8 mmol), Potassium carbonate 2.211 (4 eq, 16 mmol), Pd(PPh$_3$)$_4$ 231 mg (0.1 eq, 0.2 mmol) was dissolved in DME and water (10:1) 100 mL under nitrogen gas and remove the oxygen in −78° C. The whole solution was refluxed for 24 hours. The reaction mixture was extracted with water and 150 mL of dichloromethane (three times) organic layer was separated and was dried with MgSO$_4$. The crude residue was purified by column chromatography on silica gel (EtOAc/dichloromethane/hexane, 1/30/30). The combined organic layers were dried (MgSO$_4$), filtered, and evaporated. The crude solid was re-crystallized from CH$_2$Cl$_2$/n-hexane to afford 1570 mg of pure compound I. Spectral data as follow: T$_m$: 312° C., T$_g$: 171° C., T$_d$: 397° C. (DSC); M.W.: 546.62; $^1$H NMR (400 MHz, CDCl$_3$) δ 8.78 (d, J=1.3, 2H), 8.02 (d, J=7.7, 2H), 7.98 (dd, J=8.0, 1.7, 2H), 7.83-7.79 (m, 4H), 7.60 (d, J=1.7, 2H), 7.52 (d, J=8.0, 2H), 7.45 (td, J=6.8, 0.7, 2H), 7.33 (dd, J=8.0, 1.0, 2H), 7.29 (d, J=8.6, 2H), 7.10 (s, 2H); $^{13}$C NMR (100 MHz, CDCl$_3$) δ 159.5, 152.3, 142.3, 139.6, 139.0, 138.3, 137.1, 133.9, 133.3, 128.5, 128.1, 127.7, 126.8, 126.3, 120.7, 119.4, 116.9, 107.6, 66.2; TLC R$_f$ 0.25 (EtOAc/dichloromethane/hexane, 1/30/30); HR-MS (ESI) calcd for C$_{39}$H$_{23}$N$_4$: 547.1917. found: 547.1922; Anal. Calcd for C$_{39}$H$_{22}$N$_4$: C, 85.69; H, 4.06; N, 10.25. Found: C, 85.353; H, 4.085; N, 10.222.

Example C1

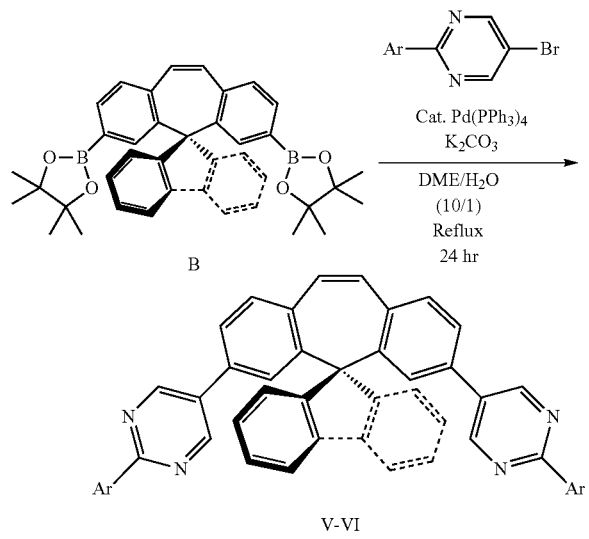

Synthetic Scheme IIB

B

V-VI

According to Synthetic Scheme IIB, intermediate B (99%) 1.783 g (1 eq, 3 mmol), 2-phenyl-4-bromoo-pyrimidine (98%) 1.24 g (2.6 eq, 7.8 mmol), Potassium carbonate 1.658 g (4 eq, 12 mmol), Pd(PPh$_3$)$_4$ 146 mg (0.05 eq, 0.15 mmol) was dissolved in DME and water (10:1) 100 mL under nitrogen gas and remove the oxygen in −78° C. The whole solution was refluxed for 24 hours. The reaction mixture was extracted with water and 50 mL of dichloromethane (three times) organic layer was separated and was dried with MgSO$_4$. The crude residue was purified by column chromatography on silica gel (EtOAc/dichloromethane/hexane, 1/15/15). The combined organic layers were dried (MgSO$_4$), filtered, and evaporated. The crude solid was re-crystallized from CH$_2$Cl$_2$/n-hexane to afford 1978 mg of pure compound V. Spectral data as follow: T$_m$: 349° C., T$_g$: 166° C., T$_d$: 389° C. (DSC); M.W.: 650.77; $^1$H NMR (400 MHz, CDCl$_3$) δ 8.69 (s, 4H), 8.40 (d, J=3.6, 2H), 8.38 (t, J=2.4, 2H), 8.05 (d, J=8.0, 2H), 7.78 (d, J=7.6, 2H), 7.54 (d, J=8.0, 2H), 7.52 (d, J=1.6, 2H), 7.50-7.47 (m, 6H), 7.44 (td, J=7.4, 0.7, 2H), 7.34 (td, J=7.6, 0.8, 2H), 7.08 (s, 2H); $^{13}$C NMR (100 MHz, CDCl$_3$) δ 163.3, 154.7, 152.3, 142.7, 138.9, 137.1, 136.7, 134.2, 133.4, 133.3, 130.7, 128.7, 128.6, 128.0, 127.9, 127.3, 126.7, 125.2, 120.7, 66.1; TLC R$_f$ 0.25 (dichloromethane/hexane, 1/1); HR-MS (ESI) calcd for C$_{47}$H$_{30}$N$_4$: 651.2543. found: 651.2556; Anal. Calcd for C$_{47}$H$_{30}$N$_4$: C, 86.74; H, 4.65; N, 8.61. Found: C, 86.643; H, 4.749; N, 8.572.

Example C2

According to Synthetic Scheme IIB, intermediate B (99%) 1.780 g (1 eq, 3 mmol), [2-(3-pyridyl-4-bromopyrimidine (98%) 1.56 g (2.2 eq, 6.6 mmol), Potassium carbonate 1.658 g (4 eq, 12 mmol), Pd(PPh$_3$)$_4$ 170 mg (0.05 eq, 0.15 mmol) was dissolved in DME and water (10:1) 80 mL under nitrogen gas and remove the oxygen in −78° C. The whole solution was refluxed for 24 hours. The reaction mixture was extracted with water and 100 mL of dichloromethane (three times) organic layer was separated and was dried with MgSO$_4$. The crude residue was purified by column chromatography on silica gel (MeOH/dichloromethane/hexane, 1/30). The combined organic layers were dried (MgSO$_4$), filtered, and evaporated. The crude solid was re-crystallized from CH$_2$Cl$_2$/n-hexane to afford 1790 mg of pure compound VI. Spectral data as follow: T$_m$: 332° C., T$_g$: 171° C., T$_d$: 397° C. (DSC); M.W.: 652.74; $^1$H NMR (400 MHz, CDCl$_3$) δ 9.60 (s, 2H), 8.70 (s, 4H), 8.64 (dd, J=7.9, 1.7, 2H), 8.05 (d, J=7.7, 2H), 7.79 (d, J=7.6, 2H), 7.54 (d, J=7.8, 2H), 7.51 (d, J=7.9, 2H), 7.46 (t, J=7.3, 2H), 7.41-7.34 (m, 4H), 7.25 (s, 2H), 7.09 (s, 2H); $^{13}$C NMR (100 MHz, CDCl$_3$) δ 161.5, 154.8, 152.2, 151.4, 149.7, 142.8, 139.0, 136.9, 135.2, 133.9, 133.5, 133.4, 132.7, 131.5, 128.8, 127.9, 127.4, 126.6, 125.4, 123.4, 66.1; TLC R$_f$ 0.3 (methanol/dichloromethane, 1/30); HR-MS (FD) Anal. Calcd for 652.2370. found: 652.2351; Anal. Calcd for C$_{45}$H$_{28}$N$_6$: C, 82.80; H, 4.32; N, 12.87. Found: C, 82.427; H, 4.337; N, 12.819.

Example D

According to Synthetic Scheme HA, intermediate B 2.0809 g (1 eq, 3.5 mmol), 2-chloro-4,6-diphenylpyrimidine 2.0542 g (2.2 eq, 7.7 mmol), Potassium carbonate 4.832 g (10 eq, 35 mmol) in water 17.5 mL, Pd(dppf)Cl$_2$ 150 mg (0.05 eq, 0.18 mmol) was dissolved in Toluene 70 mL. The whole solution was 100° C. for 36 hours. The reaction mixture was extracted with water and 50 mL of dichloromethane (three times) organic layer was separated and was dried with MgSO$_4$. The crude residue was purified by column chromatography on silica gel (dichloromethane/hexane, 1/2) to afford 1.2019 g yield 43% of pure compound with chemical formula 3.

chemical formula 3

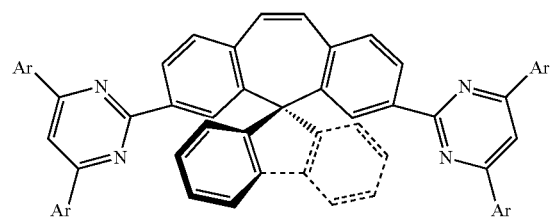

Ar in chemical formula 3 is a phenyl group. Spectral data as follow: $T_m$: 398° C., $T_g$: 195° C., $T_d$: 509° C. (DSC); M.W.: 802; $^1$H NMR (400 MHz, CDCl$_3$) δ 8.61 (d, J=1.3 Hz, 2H), 8.56 (dd, J=7.8, 14, Hz, 2H), 8.18 (d, J=7.7 Hz, 2H), 8.12 (dd, J=5.3, 4.1 Hz, 1H), 7.91 (s, 2H), 7.86 (d, J=7.6 Hz, 2H), 7.58-7.54 (m, 16H), 7.86 (t, J=6.3 Hz, 2H), 7.14 (s, 2H); $^{13}$C NMR (100 MHz, CDCl$_3$) 164.1, 163.2, 153.4, 142.0, 139.3, 138.5, 137.8, 137.2, 133.8, 132.7, 130.7, 129.6, 128.7, 127.7, 127.6, 127.2, 127.0, 120.5, 109.4, 66.6; TLC R$_f$ 0.17 (Chloroform/hexane, 1/3); High Resolution MS calcd for C$_{59}$H$_{38}$N$_4$: 802.3096. found: 802.3070.

Example E

Synthetic Scheme III

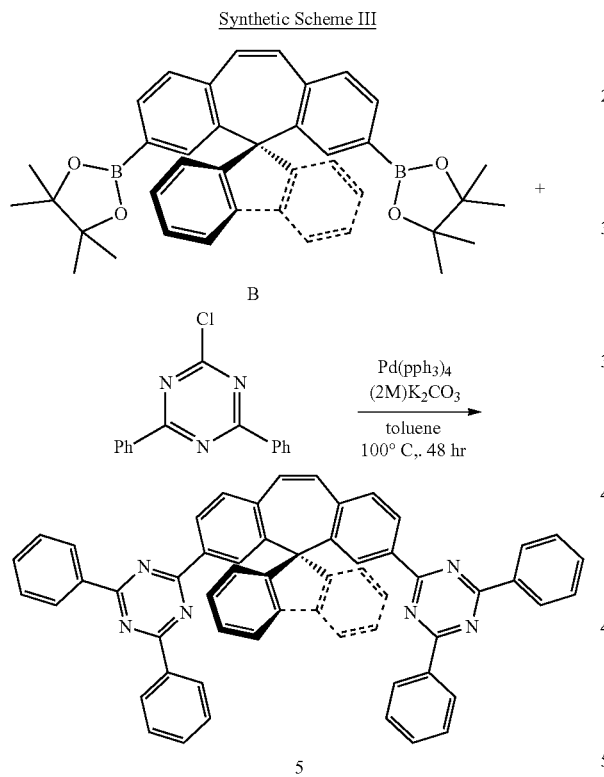

According to Synthetic Scheme III, intermediate B 3.006 g (1 eq, 5 mmol), 2-chloro-4,6-diphenyl-1,3,5-triazine 4.009 g (3 eq, 15 mmol), Potassium carbonate 6.909 g (10 eq, 50 mmol) in water 25 mL, Pd(PPh$_3$)$_4$ 200 mg (0.03 eq, 0.17 mmol) was dissolved in Toluene 100 mL. The whole solution was 100° C. for 48 hours. The reaction mixture was extracted with water and 50 mL of dichloromethane (three times) organic layer was separated and was dried with MgSO$_4$. The crude residue was purified by column chromatography on silica gel (dichloromethane/hexane, 1/2) to afford 2.012 g yield 52% of pure compound of chemical formula 5.

chemical formula 5

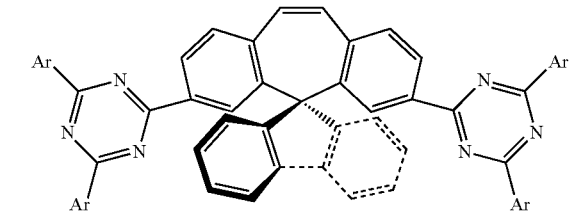

Ar in chemical formula 5 is a phenyl group. Spectral data as follow: $T_m$: 402° C., $T_g$: 201° C., $T_d$ 497° C. (DSC); M.W.: 804; $^1$H NMR (400 MHz, CDCl$_3$) δ 8.65 (d, J=1.6 Hz, 2H), 8.58-8.55 (m, 5H), 8.14 (d, J=8 Hz, 1H), 7.89 (d, J=7.6 Hz, 1H), 7.63-7.54 (m, 8H), 7.42 (dt, J=7.6 Hz, J=0.8 Hz, 1H), 7.16 (s, 1H); $^{13}$C NMR (100 MHz, CDCl$_3$) 171.2, 170.6, 152.9, 142.1, 140.1, 139.3, 136.0, 134.4, 132.9, 130.1, 128.98, 128.4, 127.8, 127.2, 120.7, 66.4; TLC R$_f$ 0.14 (Chloroform/hexane, 1/4); MS (HR-FAB) 805.6 (FAB, 100).

Although the present invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the present invention.

What is claimed is:
1. A compound is represented by general formula I:

(general formula I)

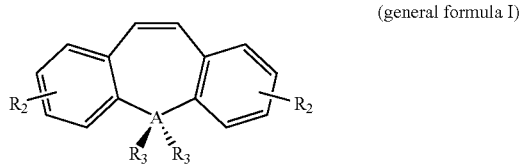

wherein A is carbon atom or silicon atom;
wherein R$_2$ is independently a triazine group, pyrimidine group or phenyl group;
when R$_2$ is a triazine group, R$_2$ is selected from the group consisting of general formula II-1-1, general formula II-1-5 to general formula II-1-19;

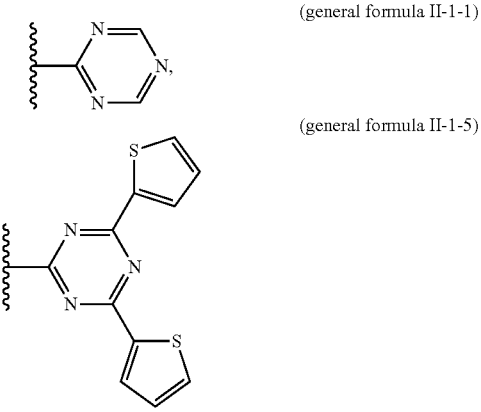

(general formula II-1-6)
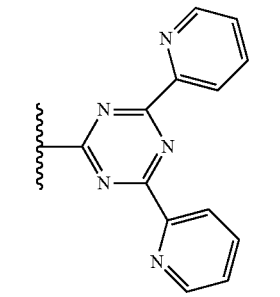
(general formula II-1-7)
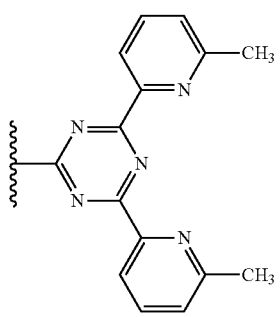
(general formula II-1-8)
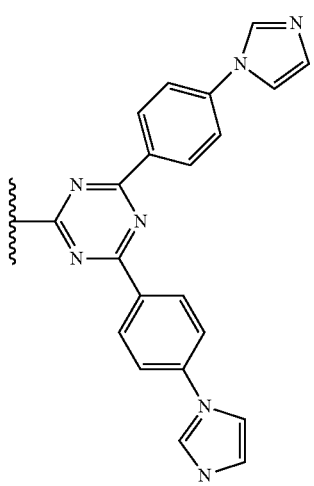
(general formula II-1-9)
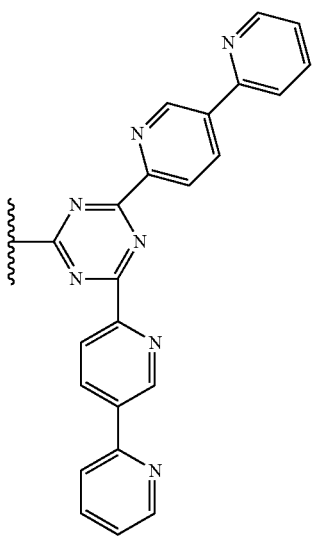
(general formula II-1-10)
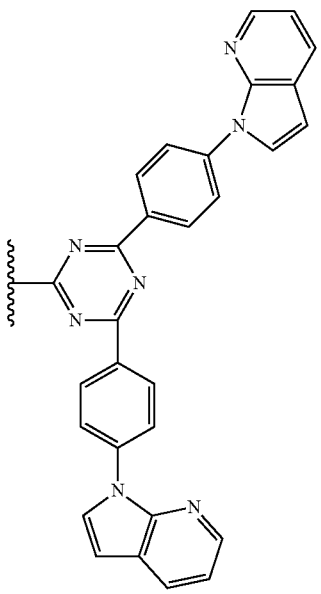
(general formula II-1-11)
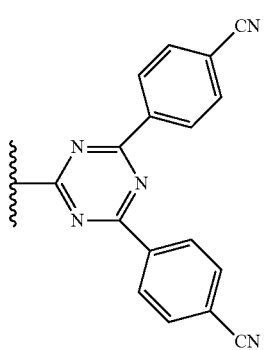
(general formula II-1-12)
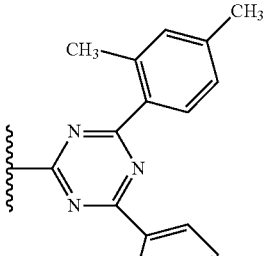
(general formula II-1-13)
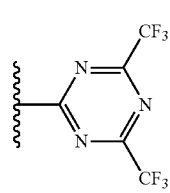

(general formula II-1-14)
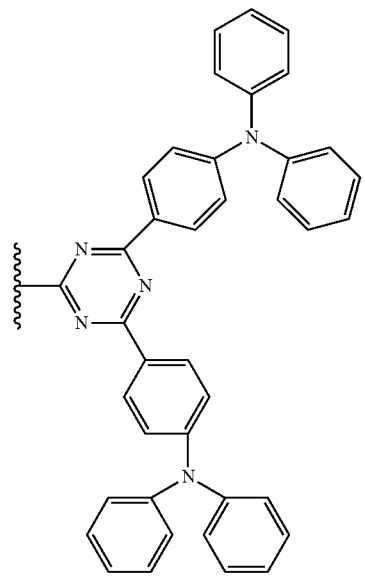
(general formula II-1-17)
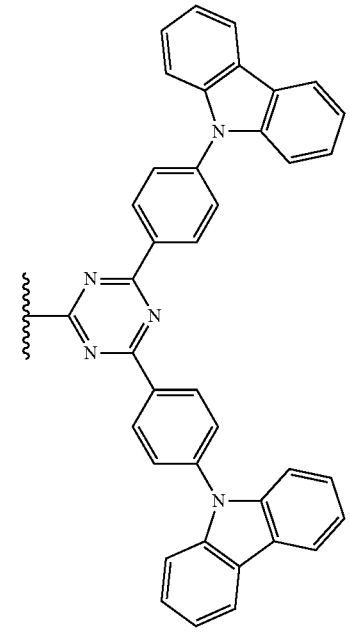
(general formula II-1-15)
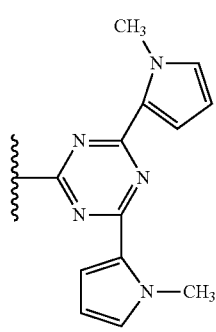
(general formula II-1-18)
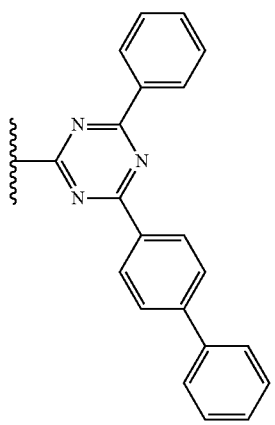
(general formula II-1-16)
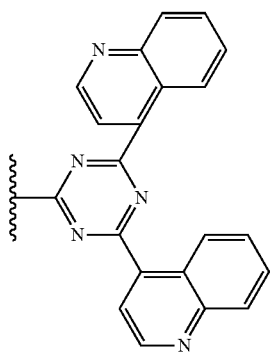
(general formula II-1-19)
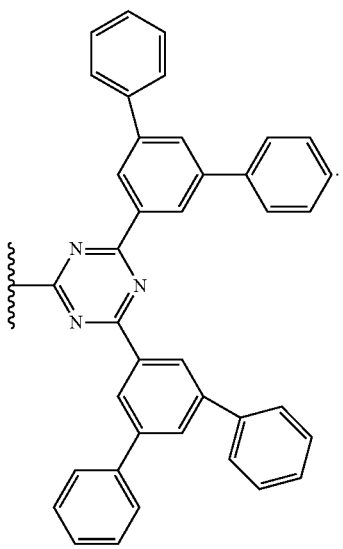

when $R_2$ is a pyrimidine group, $R_2$ is selected from the group consisting of general formula II-2-1, general formula II-2-3 to formula II-2-10;

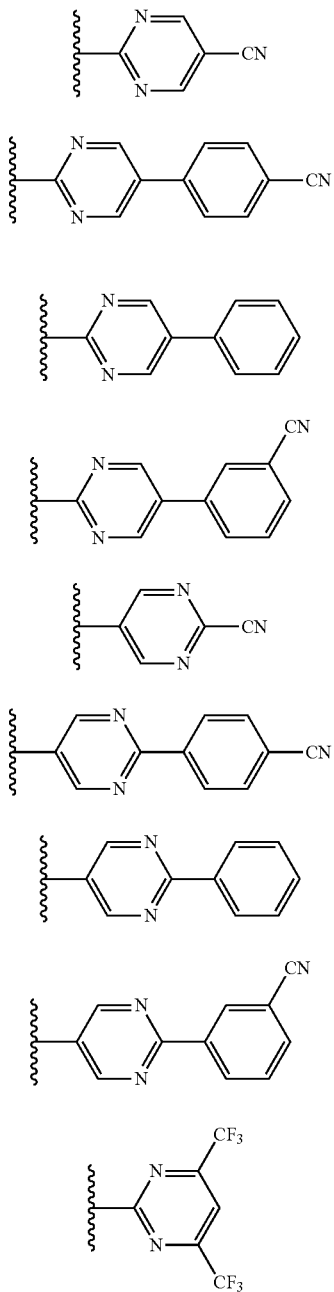

(general formula II-2-1)
(general formula II-2-3)
(general formula II-2-4)
(general formula II-2-5)
(general formula II-2-6)
(general formula II-2-7)
(general formula II-2-8)
(general formula II-2-9)
(general formula II-2-10)

when $R_2$ is phenyl group, $R_2$ is selected from the group consisting of general formula II-3-2 to general formula II-3-4;

(general formula II-3-2)

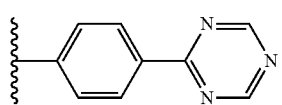

(general formula II-3-3)
(general formula II-3-4)

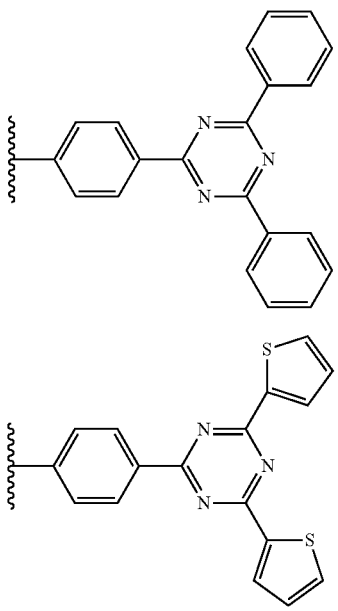

wherein $R_3$ is independently a methyl group, phenyl group, tert-butyl group or two of $R_3$ are linked by a single bond represented by general formula I-2, and (general formula I-2)

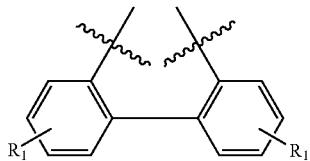

wherein $R_1$ is a hydrogen atom, tert-butyl group or naphthyl group.

2. The compound of claim 1, which is applied in an organic light emitting device (OLED) for being as a hole-blocking material and/or an electron-transporting material.

3. The compound of claim 1, wherein the compound has glass transition temperatures (Tg) ranged from 156° C. to 202° C., decompositiontemperatures (Td) ranged from 419° C. to 463° C., oxidation potentials ranged from 1.04 V to 1.16 V and redox potentials ranged from −1.75 V to −1.93 V.

4. An optoelectronic device, comprising:
a first electrode, an interlayer and a second electrode sequentially disposed on a substrate, wherein the interlayer has a compound, the compound is represented by general formula I:

(general formula I)

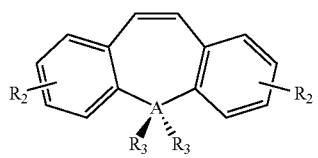

wherein A is carbon atom or silicon atom;
wherein $R_2$ is independently a triazine group, pyrimidine group or phenyl group;

when $R_2$ is a triazine group, $R_2$ is selected from the group consisting of general formula II-1-1, general formula II-1-5 to general formula II-1-19;
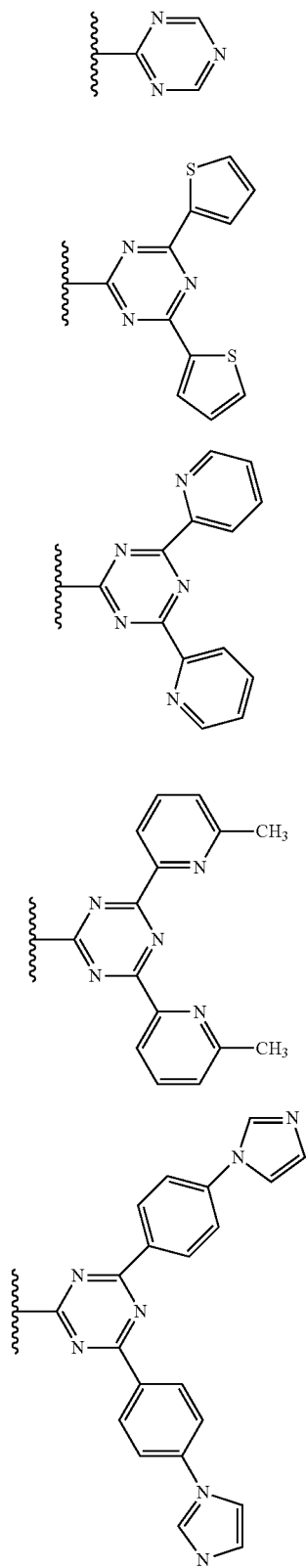
(general formula II-1-1)
(general formula II-1-5)
(general formula II-1-6)
(general formula II-1-7)
(general formula II-1-8)
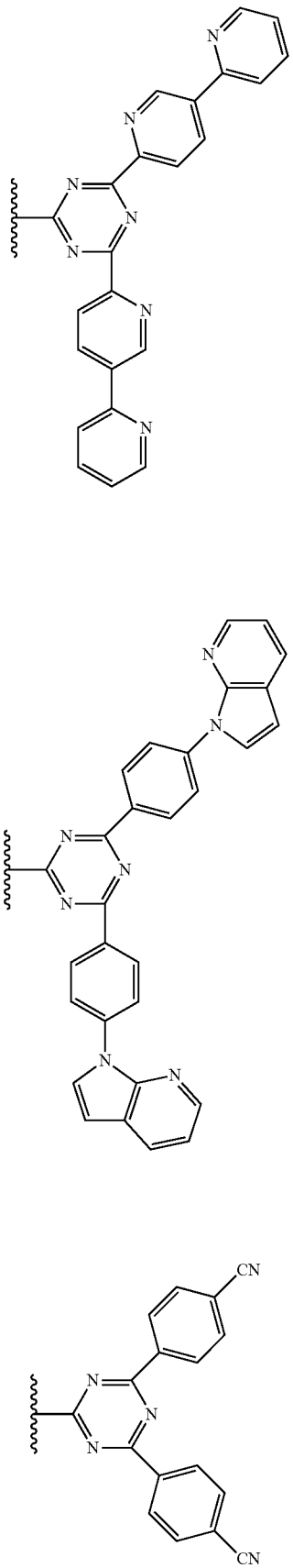
(general formula II-1-9)
(general formula II-1-10)
(general formula II-1-11)

(general formula II-1-12)
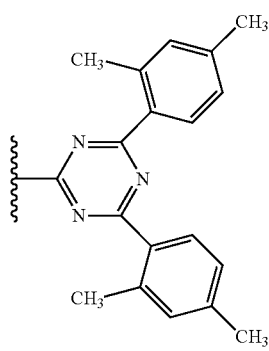
(general formula II-1-13)
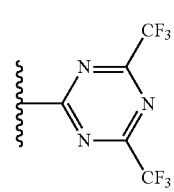
(general formula II-1-14)
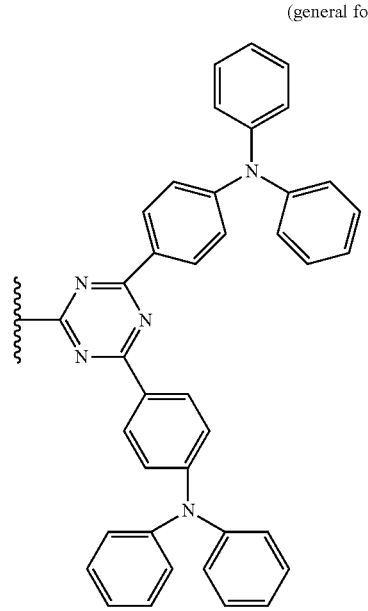
(general formula II-1-15)
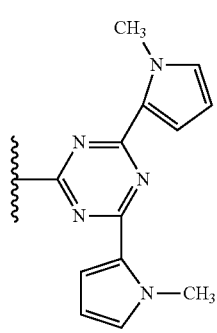
(general formula II-1-16)
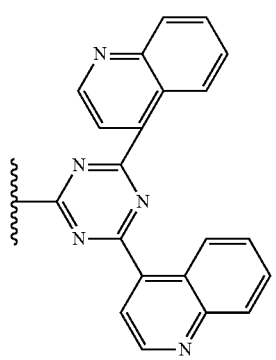
(general formula II-1-17)
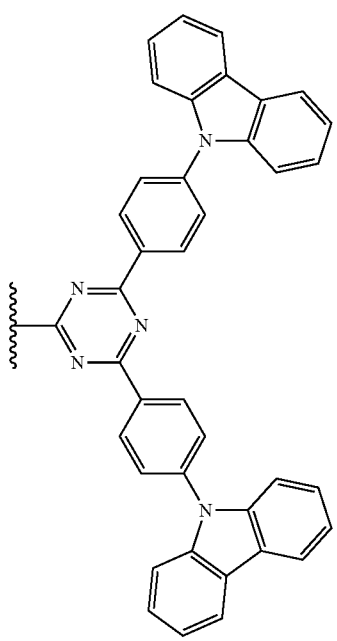
(general formula II-1-18)
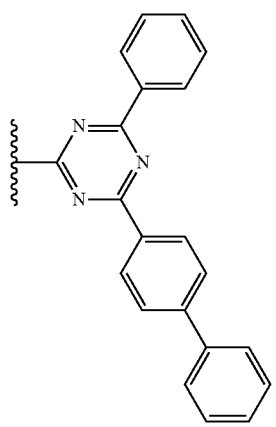

-continued (general formula II-1-19)

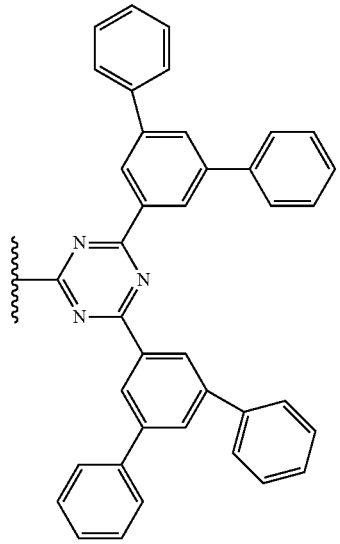

when R₂ is a pyrimidine group, R₂ is selected from the group consisting of general formula II-2-1, general formula II-2-3 to formula II-2-10;

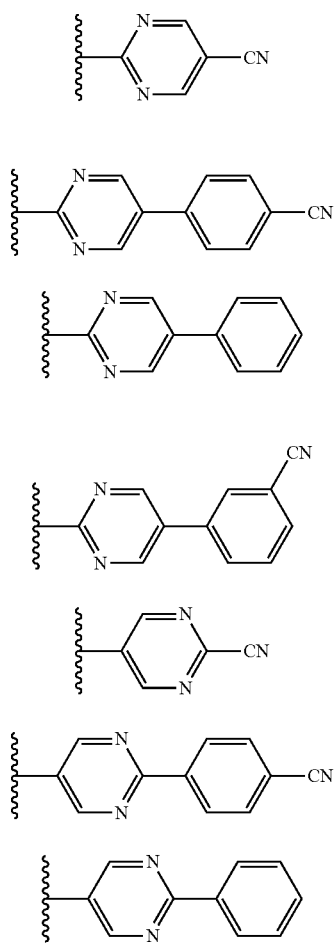

(general formula II-2-1)
(general formula II-2-3)
(general formula II-2-4)
(general formula II-2-5)
(general formula II-2-6)
(general formula II-2-7)
(general formula II-2-8)

-continued (general formula II-2-9)

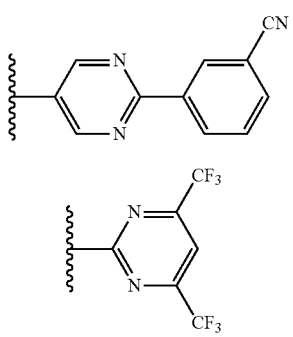

(general formula II-2-10)

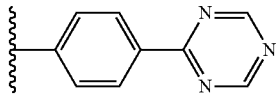

when R₂ is phenyl group, R₂ is selected from the group consisting of general formula II-3-2 to general formula II-3-4;

(general formula II-3-2)

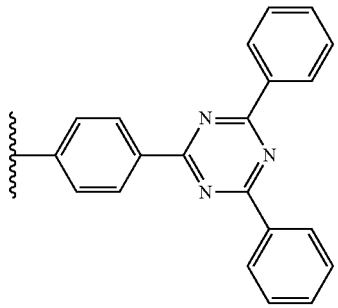

(general formula II-3-3)

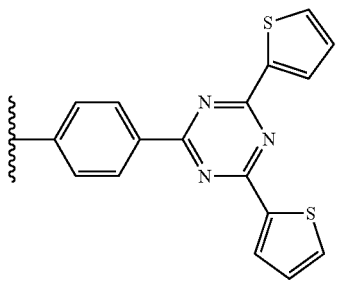

(general formula II-3-4)

wherein $R_3$ is independently a methyl group, phenyl group, tert-butyl group or two of $R_3$ are linked by a single bond represented by general formula I-2, and (general formula I-2)

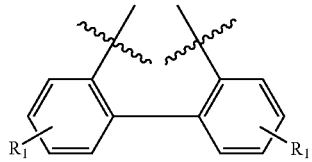

wherein $R_1$ is a hydrogen atom, tert-butyl group or naphthyl group.

5. The optoelectronic device of claim 4, wherein the optoelectronic device is an organic light emitting device (OLED), the interlayer is an electron transport layer and/or a hole blocking layer.

\* \* \* \* \*